(12) United States Patent
Talley et al.

(10) Patent No.: US 6,734,965 B2
(45) Date of Patent: May 11, 2004

(54) OPTICAL PATTERNATION METHOD

(76) Inventors: Douglas G. Talley, 41426 Terrazzo, Palmdale, CA (US) 93551; Vincent G. McDonell, 2 Sunset River, Irvine, CA (US) 92604; G. Scott Samuelsen, 19412 Sierra Calmo, Irvine, CA (US) 92612

( * ) Notice: Subject to any disclaimer, the term of this patent is extended or adjusted under 35 U.S.C. 154(b) by 53 days.

(21) Appl. No.: 09/957,444

(22) Filed: Sep. 18, 2001

(65) Prior Publication Data

US 2002/0113136 A1 Aug. 22, 2002

Related U.S. Application Data

(60) Provisional application No. 60/233,611, filed on Sep. 18, 2000.

(51) Int. Cl.[7] .......................... G01N 21/64; G01N 21/47
(52) U.S. Cl. .......................... 356/318; 356/73; 356/339
(58) Field of Search .......................... 356/73, 317, 318, 356/417, 338, 339, 341

(56) References Cited

U.S. PATENT DOCUMENTS

| | | |
|---|---|---|
| 4,071,298 A | 1/1978 | Falconer |
| 4,095,775 A | 7/1978 | Hotham |
| 4,251,733 A | 2/1981 | Hirleman, Jr. |
| 4,651,010 A | 3/1987 | Javan |
| 4,688,943 A | 8/1987 | Modarress |
| 4,696,571 A * | 9/1987 | Goldberg et al. ........... 356/336 |
| 4,868,398 A | 9/1989 | Mulcey et al. |
| 5,444,530 A | 8/1995 | Wang |
| 5,483,546 A | 1/1996 | Johnson et al. |
| 5,650,847 A | 7/1997 | Maltsev et al. |

OTHER PUBLICATIONS

P. Le Gal et al., *Laser Sheet Dropsizing of dense sprays*, Optics & Laser Technology, vol. 31, 1999, pp. 75–83.

H.M. Hertz et al, *Calibration of Imaging Laser–Induced Fluorescence Measurements in Highly Absorbing Flames*, Applied Physics B, vol. 42, 1987, pp. 97–102.

N. Farrugia et al., *LIF Imaging of Fuel Distribution in Gas Turbine Combustors*, ILASS–Europe 97, 7 pages.

D.G. Talley et al., *Accounting for Laser Sheet Extinction in Applying PLLIF to Sprays*, extended abstracts from the 8th Annual Conference on Liquid Atomization and Spray Systems, ILASS–Americas 95, May 21–24, 1995, pp. 275–278.

Doug Talley et al., *Accounting for Laser Sheet Extinction and Fluorescence Signal Attenuation in Applying PLLIF to Dense Spray Fields*, extended abstracts from the 9th Annual Conference on Liquid Atomization and Spray Systems, ILASS–America 96, May 19–22, 1996, pp. 33–37.

(List continued on next page.)

*Primary Examiner*—F. L. Evans
(74) *Attorney, Agent, or Firm*—Knobbe, Martens, Olson & Bear, LLP

(57) ABSTRACT

To measure property-specific distributions like surface area and mass concentrations, in a particle field that attenuates light passing therethrough, such as a spray or aerosol, a probe beam having a suitably selected wavelength is directed into and thereby caused to interact with the particle field. Light produced by this interaction is detected by sensors separated a distance from the beam. Extinction of the probe as it propagates through the particle field is quantified by determining the amount of light exiting the field in comparison with the amount of light entering the field. The property specific concentrations are determined from the light detected by the sensors after correcting for the extinction of the beam as well as attenuation of the light traveling the distance from the beam to the sensors. The light produced by the interaction of the probe with the particle field may include scattering, fluorescence, or both. Further, methods enable the user to determine the mass and surface area distributions of a spray or aerosol by traversing a single laser beam through the ensemble of particles to be investigated.

30 Claims, 19 Drawing Sheets

OTHER PUBLICATIONS

S.V. Sankar et al., *A planar droplet sizing technique for spray characterization*, extended abstracts from the 9$^{th}$ Annual Conference on Liquid Atomization and Spray Systems, ILASS–Americas 96, May 19–22, 1986, pp. 38–42.

S.V. Sankar et al., *Time–Resolved Measurement of Liquid Mass Distribution in a Fuel injector Spray Using an Optical Patternator*, extended abstracts from the 10$^{th}$ Annual Conference on Liquid Atomization and Spray Systems, ILASS–Americas 97, May 18–21, 1997, pp. 266–270.

G. Wang et al., *An Optical Spray Pattern Analyzer*, extended abstracts from the 10$^{th}$ Annual Conference on Liquid Atomization and Spray Systems, ILASS–Americas 97, May 18–21, 1997, pp. 261–265.

Rick Sellens et al., *Non–Orthogonal Optical Spray Pattern Analysis*, extended abstracts from the 11$^{th}$ Annual Conference on Liquid Atomization and Spray Systems, ILASS–Americas 98, May 17–20, 1998, pp. 454–457.

Jeff Su et al., *Towards Quantitative Characterization of Transient Fuel Sprays Using Planar Laser Induced Fluorescence Imaging*, extended abstracts from the 11$^{th}$ Annual Conference on Liquid Atomization and Spray Systems, ILASS–Americas 98, May 17–20, 1998, pp. 106–110.

D.G. Talley et al., *Accounting for Laser Sheet Extinction in Applying Pllif to Sprays*, presented at the 34$^{th}$ Aerospace Sciences Meeting & Exhibit, Jan. 15–18, 1996, Reno, NV, pp. 1–11.

\* cited by examiner

FIG.5A
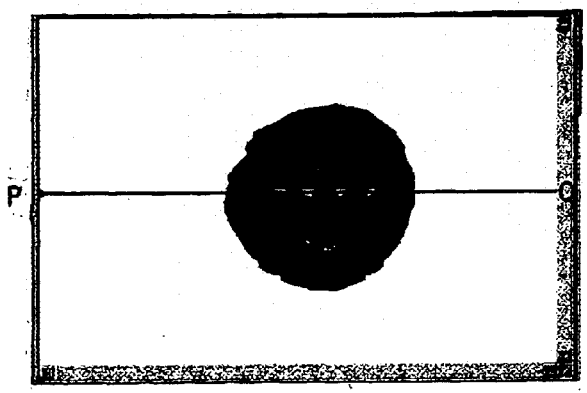 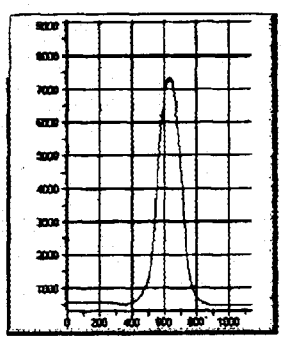
Mean: 1505.318
StdDev: 1999.688
Sum: 1732621
Y Min: 461.2636
Y Max: 7347.355
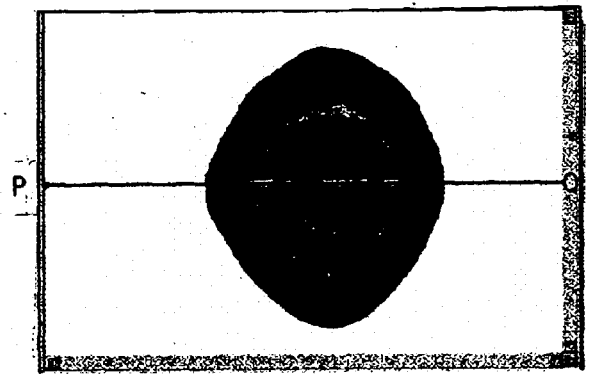 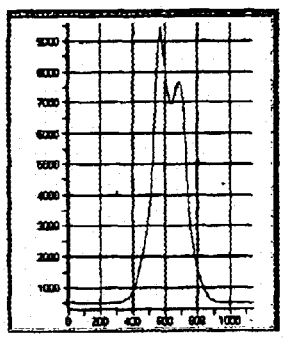
FIG.5B
Mean: 2166.546
StdDev: 2688.450
Sum: 2493694
Y Min: 506.1513
Y Max: 9417.707

Mean: 45.46451
StdDev: 13.94522
Sun: 52329.66
Y Min: 27.41818
Y Max: 61.48421

Mean: .9290609
StdDev: .0761921
Sum: 1069.349
Y Min: .6895999
Y Max: .9718860

Mean: 1.396157
StdDev: .5490475
Sum: 1604.184
Y Min: .8939429
Y Max: 2.679371

OPTICAL PATTERNATION METHOD

PRIORITY APPLICATION

This application claims priority under 35 U.S.C. §119(e) from U.S. Provisional Patent Application 60/233,611 filed Sep. 18, 2000.

This invention was made with U.S. Government support under contract No. F04611-97-C-0084 awarded by the Air Force. The U.S. Government has a nonexclusive paid-up license in this invention.

BACKGROUND OF THE INVENTION

1. Field of the Invention

The invention relates to what is referred to herein as "patternation," performing quantitative measurements of the specific properties of particles, e.g., surface area and/or mass distributions, within a particle field such as a spray, including dense particle fields. More particularly, the invention relates to an optical technique for determining such distributions.

2. Description of the Related Art

Particle fields comprising collections of particles, such as liquid particles or droplets in sprays, are encountered in many aspects of daily life. Sprays and other particle fields are associated with water sprinklers, paint sprayers, chemical process plants, medicinal coatings for tablets and pills, aerosols for inhalation therapy, lubrication, cooling, fabrication techniques using molten metals, and fuel and/or oxidizer injectors for heating and power generation, diesel and spark ignited reciprocating engines (e.g., automotive applications), gas turbine engines for air, marine, and ground applications, and rocket engines. The efficacy of the sprays in most applications depends largely on the spatial distribution of the particles, i.e., droplets of liquid, or its "pattern," produced by an atomizer. Consequently, a method that would quickly and reliably characterize this pattern has been anxiously sought for many years. Such a method could also be used for quality control in the production of atomizers.

Optical techniques for determining distributions in particle fields are attractive since they are non-invasive and generally offer relatively high spatial and temporal resolution. Furthermore, they are robust in harsh environments and can be applied in any physical orientation. An optical patternator generally involves the use of laser light which is directed into the particle field being investigated. In one optical patternator technique, laser light is tuned to an absorption peak in molecules which are either inherent in the field or have been added as dopants. The molecules fluoresce at a wavelength other than that of the incident light in a process known as laser induced fluorescence (LIF). The LIF is detected by an optical detector, which is usually positioned some distance from the sample. The amount of light emitted from a given volume in the particle field is proportional to amount of light incident upon that volume, and the total number of emitting molecules in the volume. The total number of emitting molecules will in turn be proportional to the total amount of mass in the volume, regardless of whether this mass is contained in one particle or whether the mass is distributed over several particles in the volume. An "amount of light" is defined herein to mean the total light energy crossing a surface over a given period of time. For a continuous light source, the given period of time may be more or less arbitrarily chosen. For a pulsed light source, the given period of time is the duration of the pulse. Similarly, an "amount of signal" or "signal amount" is defined herein to mean the total signal energy crossing a surface over a given period of time. The terms "scattered signal" or "LIF signal" may sometimes be used herein to distinguish the scattered light and the LIF light from the original excitation light.

In another optical patternator technique, laser light scattered by particles in the field is collected. This scattered light is not shifted in wavelength, and the amount of scattered light is proportional to the amount of incident laser light. Under certain conditions, particularly when the particles are spherical and the wavelength of the light is much smaller than the size of the particles, the amount of scattered light can also be proportional to the total surface area of the particles contributing to the scattering.

Optical patternation techniques, however, generally suffer from shortcomings related to the scattering of light. For example, whereas the amount of scattered light can sometimes be theoretically related to the total surface area in a volume of the particle field, and whereas the amount of LIF emitted from a volume in the particle field is theoretically related to the amount of mass in the volume, the amount of detected scattering and/or LIF signal is not in general proportional to the area or mass distribution for at least the following reasons. First, the particle field to be investigated will scatter and/or absorb some of the incident laser light, e.g., at the surfaces of the particles. If enough particles are present, the amount of the exciting laser light can be considerably reduced, resulting in an under-representation of the amount of material that is actually present. This effect is referred to herein as "extinction" of the incident laser beam. Secondly, some of the emitted LIF and/or scattered light will be reabsorbed and/or scattered by particles within the field before reaching the optical detector, leading to a further under-representation of the amount of material that is actually present. This phenomenon is referred to herein as "signal attenuation." Third, light scattered by particles illuminated by the laser strike other particles not directly illuminated by the laser. These other particles also scatter and/or fluoresce, adding an unknown amount of additional signal from locations other than at the measurement point, in an effect referred to herein as "secondary emission."

Thus, there is an need for improved methods of accurately determining property-specific distribution such as the surface area and/or mass distributions of particle fields.

SUMMARY OF THE INVENTION

In one aspect of the invention, to measure property-specific distributions like surface area and mass concentrations in a particle field that attenuates light passing therethrough, such as a spray or aerosol, a probe beam having a suitably selected wavelength is directed into and thereby caused to interact with the particle field. Light produced by this interaction is detected by sensors separated a distance from the beam. Extinction of the probe as it propagates through the particle field is quantified by determining the amount of light exiting the field in comparison with the amount of light entering the field. The property specific concentrations are determined from the light detected by the sensors after correcting for the extinction of the beam as well as attenuation of the light traveling the distance from the beam to the sensors. In various embodiments, the light produced by the interaction of the probe with the particle field may include scattering, fluorescence, or both. Also, in preferred embodiments, the property-specific concentrations can be characterized in a plane of interest, a portion that is thin with respect to the particle field. The sensors can be located within a plane passing through and parallel to the plane of interest. Accordingly, large volumes of the particle field need not be sampled in addition to the plane of interest in order to determine the accurate particle-specific distributions within the plane of interest. Further embodiments enable the user to determine the distributions of a spray or aerosol by traversing or sweeping a narrow laser beam, such as a gaussian beam or a beam having a circularly symmetric cross-section, i.e., largely cylindrical in shape, through the portion of the ensemble of particles to be characterized. Minimizing the size of the scanning beam to coincide with the field imaged by the sensors can reduce the effects of secondary emission. In addition, in various embodiments of the invention, distributions of properties of particle fields including non-spherical particles can be obtained.

Another aspect of the invention comprises a method of determining a property distribution in a collection of particles. In this method, a beam of excitation light is directed into the collection or ensemble of particles and propagated along a specific optical path within the collection of particles. Scattering and/or fluorescence such as laser induced fluorescence (LIF) from particles along the optical path is produced by the excitation light, the particles additionally scattering and otherwise diminishing or extinguishing the excitation light propagating along said optical path. Measurements of the amount of excitation light entering and exiting the collection of particles are performed and compared to determine the extent to which the excitation light is extinguished by the collection of particles. Scattering and/or fluorescence signals originating from various points along the optical path is determined with detectors thereby detecting the respective scattering and/or fluorescence signals, the scattered and/or fluorescence signals undergoing additional scattering and absorption as they propagate away from the optical path and towards the detectors used to detect the signals. The property distribution of the particles is computed along the optical path using the scattering and/or fluorescence signals, while accounting for the extinction of the excitation light propagating along the optical path, and while accounting for attenuation of the scattered and/or fluorescence signals.

BRIEF DESCRIPTION OF THE DRAWINGS

FIGS. 5A and 5B are two-dimensional plots derived from scatter and fluorescence signals, $\tilde{E}'_S(x,y)$, $\tilde{E}'_F(x,y)$, respectively, at the detectors as the particle field is translated through a fixed laser beam, the 2D plots corresponding to the sheet through the particle field (also shown is a line plot showing values along the line P-Q in the plots);

DETAILED DESCRIPTION OF THE PREFERRED EMBODIMENT

Distributions of specific properties within a particle field can be determined by probing the particle field with a beam of light and detecting the interaction of this light with the particles in the field. Examples of such specific properties include but are not limited to surface area and mass divided by the volume detected by the detectors. The surface area or mass divided by the volume detected by the detectors will be referred to herein as the "mass concentration" or the "surface area concentration," respectively. Special techniques for removing the effects of beam extinction, signal attenuation, and secondary emission permit quantitative results of the property specific distributions to be obtained.

Scattering and laser induced fluorescence can result in certain cases when an optical beam is passed through a particle field. Scattering corresponds to scattering of the incident light by the particles; the wavelength of the scattered light is the same as that of the incident light. In contrast, an incident light beam can result in fluorescence such as laser induced fluorescence (LIF) if the incident beam is tuned to an appropriate "resonant" wavelength. The particle fluorescing will emit light having a wavelength shifted with respect to the wavelength of the incident light beam.

The amount of an LIF signal is proportional to the amount of the incident light beam and the number of emitting molecules. Mass concentration measurements are possible because the number of emitting molecules is proportional to the mass in the volume detected by the detectors. When the particle are spherical and are much larger than the wavelength of the light, the intensity of the scattered light is proportional to the surface area of the particles.

Figure 1A:
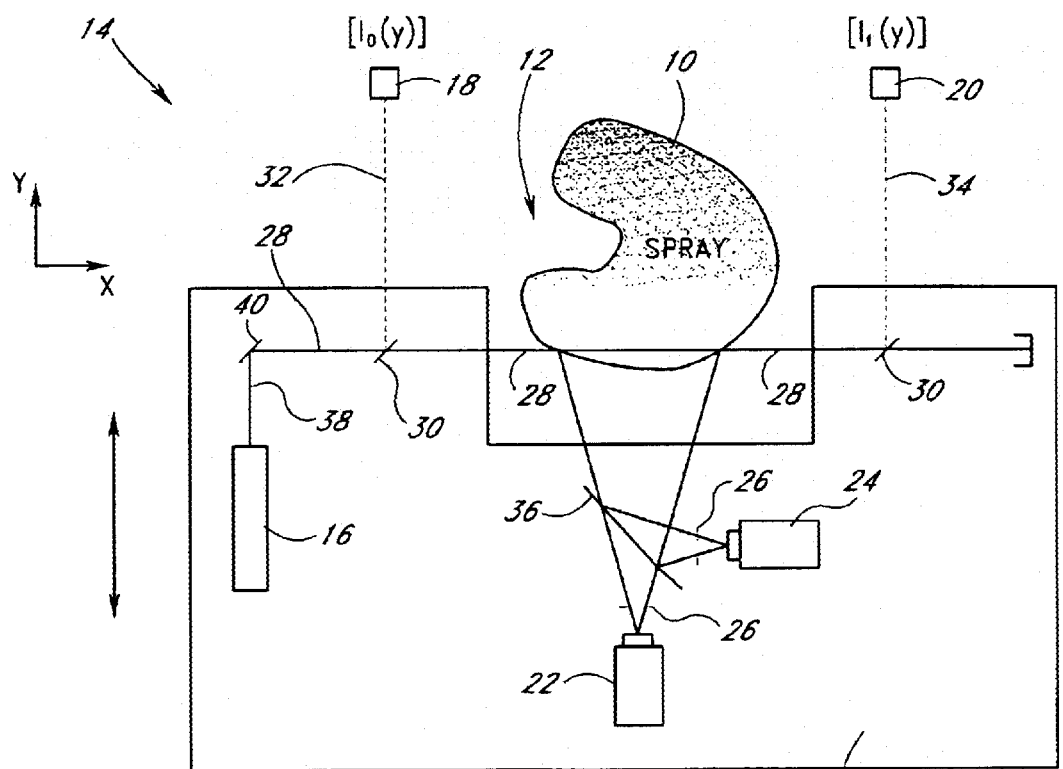
FIG. 1A is a schematic drawing depicting one embodiment of an apparatus for characterizing property-specific distributions such as surface area and mass distributions of particle field.

In one preferred embodiment for measuring property-specific distributions such as surface area or mass illustrated in FIG. 1, a particle field 10 comprising a collection of particles such as droplets of liquid is ejected from a nozzle (not shown) into a region 12 where the particle field can be analyzed. A system 14 for characterizing the particle field includes a light source 16, power monitors 18, 20 for quantifying intensity of light emitted from the source at locations on opposite sides of the particle field 10, as well as two detectors 22, 24 with wavelength selective filters (not shown) and spatial filters 26 in front of each.

The light source 16 in this example comprises a laser, which may be pulsed or continuous wave (CW). In some embodiments, this light source emits light having a single polarization state. An optical path 28 extends from the laser 16 through the region 12 where the particle field 10 is analyzed. Beamsplitters 30 are inserted in the optical path 28 on opposite sides of the particle field 10 such that separate optical paths 32, 34 to these power monitors 18, 20 are provided. The two detectors 22, 24 are located at positions where the particle field 10 can be imaged. In this example, these two detectors 22, 24 comprise 2D detectors arrays fitted with imaging optics for forming images on the detector arrays. In another embodiment, linear arrays may be employed. A partially reflective mirror 36 is included to allow the two detectors 22, 24 to image a similar portion of the particle field 10. In another embodiment, a single detector 22 may be used and the partially reflective mirror 36 removed, if the particle field is sufficiently steady if time-averaged such that a scattered signal and the fluorescence signal can be alternately recorded by alternately changing the filters (not shown) in front of the detector 22. In another embodiment, an image splitting optic can be used in conjunction with a single 2D detector 22 and spectral filters so that the scattered signal and fluorescence signal can be recorded simultaneously on one 2D detector. Other configurations can also be employed to record optical signals emanating from the particle field simultaneously or over a sufficiently short duration.

A single laser beam 38 emitted from the laser 16 is directed from one direction into the particle field 10 and passes therethrough. Some of the light within this beam 38 is scattered by particles within the particle field 10; some of the light in this beam causes particles within the field to fluoresce. The two detector arrays in the detectors 22, 24 record fluorescence and elastic scattering signals, respectively, with the aid of the partially reflecting mirror arrangement. The spectral filters placed in front of the detector arrays isolate the appropriate wavelengths, and the spatial filters 26 comprising masks block out secondary emission comprising secondary fluorescence and secondary scattering. These masks can prevent a light originating from portions of the particle field from reaching the detector and being detected. Portions of the particle beam that may be blocked may include the background surrounding the optical path over which the beam travel, or portions of the optical path itself. As discussed above, in one of many alternative arrangements, a detector array can be used to detect both signals with the help of a method to repeatedly change filters and detector gains is used. The two detectors on opposite sides of the particle field 10 may comprise photomultiplier tubes (PMTs) or other sensitive detectors, which together enable the beam extinction, i.e. the amount that the light in the laser beam 38 is reduced as it passes through the particle field, to be measured.

One beamsplitter 40, reflects the beam emitted by laser 16 to the region where the particle field 10 is analyzed and thereby controls the path 28 of the laser beam 38 through the particle field. This path 28 is parallel to a first direction corresponding to one axis on an x-y coordinate system 44, the x-axis. Much of the optics, including the beamsplitter 40 and the detectors 22, 24 are mounted on a translator 42 configured to shift the beamsplitter in an orthogonal direction parallel to the other axis, i.e. the y-axis. Accordingly, the laser beam 38 traverses an optical path 28 directed parallel to the x-axis through the particle field 10; however, the optical path itself can be traversed in a perpendicular direction which is parallel to the y-axis. In this manner, the laser beam 38 can be swept in the y direction so as to map out a planar sheet extending through the particle field 10. The detectors 22, 24 are also translated by the same amount as the laser beam 38 and its optical path 28 through the particle field 10 such that the optical path remains in focus.

To characterize the distribution of surface area and/or mass, the laser beam 38 is transmitted through a plurality of optical paths, one such optical path 28 is shown in FIG. 1. The optical path 28 is translated in the y direction to enable the beam 38 to pass through and sample different portions of the particle field 10 located within the same plane. Fluorescence and elastic scattering data are obtained while traversing the single laser beam 38 through a plane, i.e., the sheet, in the particle field 10. In addition, the amount of light in the laser beam 38 is measured before it enters the particle field 10 and well as after it exits the particle field using the two power monitors 18, 20, for each position of the beam along the y axis. As the traverse is completed, a two-dimensional map of raw data, i.e., the amount of scattering and LIF signal collected by the detectors 22, 24, is obtained. In cases where the fluorescing characteristic of the particles is subject to change with time (i.e., the concentration of fluorescing molecules changes due to, for example, settling in a supply tank or ablation) it can be monitored using a flow cell in which a quantity of the material interrogated is excited and its emissions monitored using a detector. The signal from that detector can be used to account for variations in the fluorescing characteristics at each y position.

In practice, there may be advantage in collecting the fluorescence and scattering signals from an angle other than 90 degrees to the optical path 28 of the laser beam 38. Practical limitations, for example, may not allow the optical access necessary to collect the signals at 90 degrees. Collecting signals at angles other than 90° may increase the elastic scattering signal, allowing the laser intensity to be decreased, which would be advantageous in reducing the effects of secondary emission. However, the fluorescence signal would also decrease, and the beam path may exceed the depth of field of the imaging optics. Such issues can be dealt with within limitations that grow as the deviation from 90 degrees increases. Therefore, the collection angle will be assumed here to be 90 degrees, although the methodology described above can be applied with increasing difficulty as the collection angle deviates from 90 degrees.

As shown in the FIG. 1, fluorescence and scattering detected when the laser beam 38 is passed through portions of the particle field 10 farther from the detectors 22, 24 the will appear dimmer due to signal attenuation. Corrections to address this effect are therefore applied. The raw data collected will be a function of the amount of light in the laser beam 38, which in general will vary in the transverse direction x due to laser extinction. The raw data will also depend on the amount of signal attenuation as well as the total surface area in the case of the scattered signal, and the total mass in the case of the fluorescence signal associated with the region 12 being characterized.

In calculating the distributions for mass and surface area, the following assumptions are made:

1. Elastic scattering is the dominant mechanism causing laser extinction, i.e., the reduction in intensity of the laser beam 38, and signal attenuation, the decrease in the scattered and fluorescent signals incident on the detectors 22, 24.
2. The scattering is isotropic at any given point, i.e., the scattering is dependent only on the direction and properties of the incident light with respect to the media, not the orientation of the media. This restriction applies only on a point by point basis, not to the particle field 10 as a whole.
3. The scattering coefficients are the same at both the incident wavelength and at the wavelength of the fluorescence.
4. The detected scattering and fluorescence signals are dependent on the amount of incident light and the scattering and fluorescence cross sections, respectively, as given in general form in equation (2) below, and as given specifically for scattering and fluorescence in equations (8) and (9) below, respectively.

If the mass concentration distribution is to be determined, then both scattering and fluorescence signals must be collected since scattering is assumed to be the dominant mechanism causing laser extinction and signal attenuation. In contrast, if only the surface area concentration distribution is to be determined, then the fluorescence signal need not be collected. In the case where only the mass concentration distribution needs to be determined, then although the scatter signal is collected, it is to be related only to the scattering cross-section, i.e., the scattering cross-section need not be related to the surface area. As a consequence, in this special case, the particles need not be spherical. Mass concentration distributions of fields containing non-spherical particles can therefore be derived.

Invoking a mathematical treatment of the measurements, extinction coefficients characterize the extinction of light as it propagates through the particle field as follows:

$$\bar{\xi}(p) = \sum_n \bar{\xi}_n(p), \quad (1)$$

where $\bar{\xi}(p)$ is the total time-averaged extinction coefficient along a path for a given state of polarization in the illuminating light, where p is the distance along the path.

$\bar{\xi}_n(p)$ is the time-averaged extinction coefficient for spectral band, n, for a given state of polarization, along path p.

The spectral band will be determined by the physical mechanisms governing scattering and fluorescence, and the wavelength selective spectral filter in front of the detector array in the detector will be set to correspond to the appropriate spectral band. The recorded signals are assumed to be functionally dependent on various factors as follows:

$$\tilde{E}'_n(p) = k_n e_b(p) \bar{e}_c(p) \bar{\xi}_n(p), \quad (2)$$

where $\tilde{E}'_n(p)$ is the ratio of the detector response to incoming radiation for a given spectral band, n, along a path, p, to the total amount excitation illumination entering the particle field 10.

$k_n$ is a constant associated with the spectral band, n $e_b(p)$ is the time averaged excitation beam extinction function along a path, p $\bar{e}_c(p)$ is the time averaged signal attenuation function along a path, p $\bar{\xi}_n(p)$ is the time-averaged extinction coefficient for spectral band, n, along a path, p.

$$1 - e_{bf} = \int_{p_o}^{p_f} \sum_n [\tilde{E}'_n(p)/k_n \bar{e}_c(p)] dp, \quad (3)$$

where $e_{bf}$ is the measured total beam extinction function between the entry to the field being interrogated, denoted by $p_o$, and the exit of same, denoted by $p_f$ for all spectral bands along path p.

$\bar{e}_c(p)$ is the signal attenuation function which takes different forms depending on the limiting case chosen. In its simplest form, where the size of the collection area of the detector array, which may be determined by the optics in the detector, is small enough and the detector is far enough away so that all signals from the measuring points within the particle field to the detector are essentially directed in the same direction, the expression for $\bar{e}_c(p)$ is $$\bar{e}_c(p) = \exp\left[-\int_0^{|\vec{x}_d - \vec{x}_{f,pv}|} \bar{\xi}(\vec{x}_{f,pv} + s\hat{n}_{fd}) ds\right]. \quad (4)$$

where $\vec{x}_d$ is the location of the detector, $\vec{x}_{f,pv}$ is the location of the measuring point, $\hat{n}_{fd}$ is a unit vector describing the direction from $\vec{x}_{f,pv}$ to $\vec{x}_d$, and s is the distance in that direction. The beam extinction is related to the signal at the detector as follows:

$$1 - e_b(p) = \int_{p_o}^{p} \sum_n [\tilde{E}'_n(p)/k_n \bar{e}_c(p)] dp, \quad (5)$$

where $e_b(p)$ is the beam extinction function along path p.

As discussed above, probing a particle field with a beam of light and detecting the interaction of the beam with the field can enable the distribution of the particle property of interest to be mapped out. The relationship of the time averaged particle property of interest and the extinction coefficient associated with the particle property of interest is given by the following equation:

$$\bar{\zeta} = k_\zeta \bar{\xi}_\zeta, \quad (6)$$

where $\bar{\zeta}$ is the time averaged particle property of interest (e.g., surface area concentration, a, or mass concentration, $\rho$)

$\bar{\xi}_\zeta$ is the extinction coefficient associated with the particle property of interest (scattering, e.g., might be associated with surface area, fluorescence might be associated with mass)

$k_\zeta$ is a constant associated with the particle property of interest.

It is assumed that $k_\zeta$ is either known, or it is acceptable to know the distribution of the particle property of interest only to within an unknown constant. Note that $\bar{\xi}_\zeta$ may not be any of the band coefficients that contribute significantly to $\bar{\xi}$. Further note that it is not necessary to know which particle properties are responsible for any of the band coefficients which contribute significantly to $\bar{\xi}$, as long as the band coefficient $\bar{\xi}_\zeta$ of the particle property of interest is known. For example, if scattering is the dominant extinction mechanism, but $\bar{\xi}_\zeta$ is the fluorescence band coefficient, then only the scattering coefficient needs to be determined. It is not necessary to have an equation like equation (6) to relate the scattering coefficient to any particle property. Consequently, $\bar{\xi}_\zeta$ can be determined even if the particles are non-spherical, and no clear relationship between the scattering coefficient and the particle surface area is apparent.

Spectral filters can be used to isolate the spectral bands of particular interest and additional particle properties can be calculated. Invoking the assumption above that scattering is the dominant mechanism of extinction, Equations (1) through (5) can be rewritten as:

$$\bar{\xi}(p) = \bar{\xi}_S(p) \quad (7)$$

$$\tilde{E}'_S(p) = k_s e_b(p) \bar{e}_c(p) \bar{\xi}_S(p) \quad (8)$$

$$\tilde{E}'_F(p) = k_F e_b(p) \bar{e}_c(p) \bar{\xi}_F(p) \quad (9)$$

$$1 - e_{bf} = \frac{1}{k_S} \int_{p_o}^{p_f} [\tilde{E}'_S(p)/\bar{e}_c(p)] dp \quad (10)$$

$$\bar{e}_c(p) = \exp\left[-\int_0^{|\vec{x}_d - \vec{x}_{f,pv}|} \bar{\xi}_S(\vec{x}_{f,pv} + s\hat{n}_{fd}) ds\right] \text{ and} \quad (11)$$

$$1 - e_b(p) = \frac{1}{k_S} \int_{p_o}^{p} [\tilde{E}'_S(p)/\bar{e}_c(p)] dp \quad (12)$$

where subscripts S and F are used to denote "scattering" and "fluorescence", respectively. Equations (7)–(12) constitute a set of six equations with the seven unknowns $\bar{\xi}$, $\bar{\xi}_S$, $\bar{\xi}_F$, $e_b$, $\bar{e}_c$, $k_S$, and $k_F$, which is therefore sufficient to determine all the unknowns except $k_F$. In particular, the scattering coefficient will be determined, but the fluorescence band coefficient will be known only to within a constant. If the fluorescence is proportional to the particle mass concentration, this means that the mass concentration distribution will also be known to within a constant. Note that the mass distribution can be known to within a constant whether or not the scattering coefficient can be related to the surface area. Thus the particles need not be spherical. If the scattering coefficient is in fact proportional to the surface area concentration, then the surface area concentration distribution will also be known to within a constant. For spherical particles in the geometric optics regime, it is well known that the surface area concentration at any point will in fact be twice the scattering coefficient. Also, if the scattering coefficient is proportional to the surface area concentration, then dividing eq. (9) by eq. (8) gives:

$$\frac{\tilde{E}'_F}{\tilde{E}'_S} = \frac{k_F}{k_S} \frac{\bar{\xi}_F(p)}{\bar{\xi}_S(p)} = K D_{32}(p) \quad (13)$$

where $D_{32}(p)$ is a factor of K or $(k_\rho/k_a)$ times the Sauter mean diameter. The second equality will be true only if the scattering cross section $\bar{\xi}_S(p)$ is proportional to the surface area, which will generally require the particles to be spherical.

The algorithm based on the above described system of equations can be solved iteratively as the optical path 28 is traversed through the particle field 10 by translating the laser beam 38 and all other optics from optical paths proximal to the detectors 22, 24 toward optical paths further into the field. Consider the first row $y_1$ where the scattering and fluorescent signals are detected. Because no portion of the particle field 10 precedes this row, the time averaged signal attenuation function is known to be unity all along the row, $\bar{e}_c(p,y_1)=1$, and is therefore considered to be known. Henceforth, the variable "p" along the beam will be replaced with the variable "x," in order to more closely conform to the Cartesian notation 44 in FIG. 1.

With $\bar{e}_c(x,y_1)$ known to be equal to 1, then $k_S$, the constant associated with the scattering coefficient, can be calculated using equation (10). Then at the point $x_1$ where the beam first enters the particle field, $\bar{e}_b(x_1,y_1)$ is known to be one, so it will be possible to use equation (8) to calculate $\bar{\xi}_S(x_1,y_1)$. With $\bar{\xi}_S(x_1,y_1)$ known, it will be possible to calculate $\bar{e}_b(x_2,y_1)$ using equation (12). Then with $\bar{e}_b(x_2,y_1)$ known, $\bar{\xi}_S(x_2,y_1)$ can be calculated, and so on, in a chain-like fashion, until $\bar{e}_b(x,y_1)$ and $\bar{\xi}_S(x,y_1)$ are known along the entire row $y_1$. With $\bar{e}_b(x,y_1)$ and $\bar{e}_c(x,y_1)$ now known, $\bar{\xi}_F(x,y_1)$ can now be calculated to within a constant $k_F$ at every point along the row using equation (9). Finally, the surface area concentration $a(x,y_1)$ and mass concentration $\rho(x,y_1)$ can be calculated using versions equation (6) for each variable, namely $$a(x,y_1) = k_a \bar{\xi}_S(x,y_1) \qquad (14)$$

$$\rho(x,y_1) = k_\rho \bar{\xi}_F(x,y_1) \qquad (15)$$

provided these relationships are true. The system of equations is now solved for the first row.

The signal from the second row $y_2$ will in general be subject to some signal attenuation from the proceeding row. However, the time averaged signal extinction function $\bar{e}_c(x,y_2)$ can now be calculated using equation (11), because $\bar{\xi}_S(x,y_1)$ will already have been calculated in the first row. With $\bar{e}_c(x,y_2)$ now known, all the other variables in the second row can now be calculated as described in the previous paragraph. Each subsequent row proceeds similarly, with the time averaged signal extinction function $\bar{e}_c(x,y)$ being successively computed from the solutions to the previous rows, until the last row is reached, and the solution is complete. TABLE 1 summarizes the equations employed in calculating the relevant values for the first and remaining rows in the particle field. The equations listed in TABLE 1 are relevant to the case where the specific property of interest is area $a(x,y)$ and mass $\rho(x,y)$. The probe path 28 is coincident with the x axis and is traversed in the y axis. Note that translation in the z axis perpendicular to the x and y axis, is not necessary.

Figure 1B:
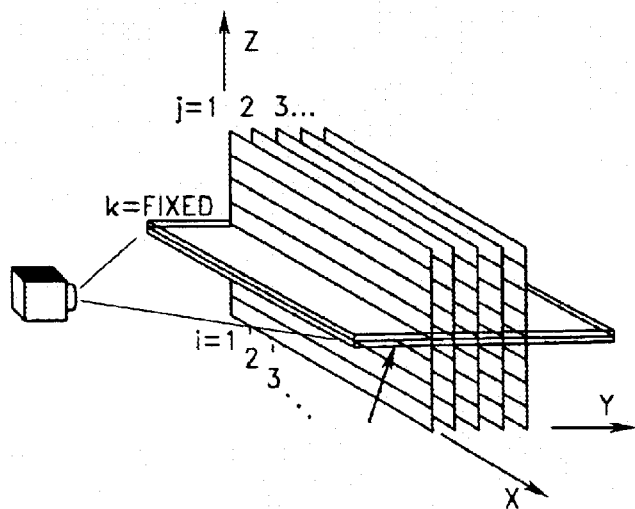
FIG. 1B is a schematic drawing depicting the orientation of the detector with respect to the particle field.
Figure 2A:
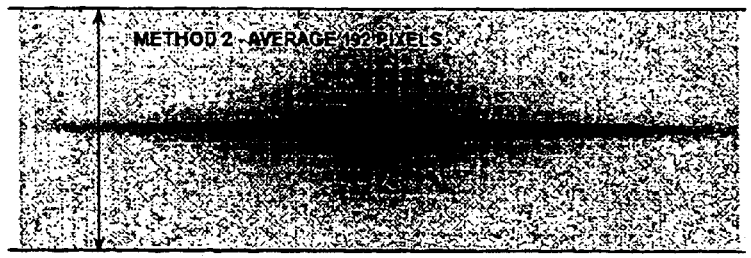
FIGS. 2A–2D show the intensity distribution across the two-dimensional detector array to illustrate how such intensity distributions at the detector array can be converted into strings of values useful for constructing distributions of a specific property throughout a sheet passing through the particle field formed from a sequence of laser beams.

FIG. 1B shows a configuration for obtaining the data to complete the calculations described above. A 2D detector images slices of a planar contiguous sub-volume of the particle field 10. The detector(s) 22, 24 is (are) located in the same plane. The measured quantities include $\tilde{E}'_S(x,y)$, the signal detected using appropriate band pass filter tuned to the wavelength of the scattered light divided by the amount of light $E_b^0$ entering the particle field, $\tilde{E}'_F(x,y)$, the signal detected using appropriate band pass filter tuned to the wavelength of the fluorescence, divided by the amount of light $E_b^0$ entering the particle field as well as the $e_{bf}$, which equals $E_b^f/E_b^0$ or the ratio of amount of light exiting the particle field to that entering it at each y position.

detector 22, 24 comprises a two-dimensional array, having, e.g., n lines and m columns, the distribution of the amount of signal across this two-dimensional array, shown in FIGS. 2A–2D, is processed to generate a single string of values corresponding to points along one optical path 28. Various methods can be employed to convert the amount of signal at each of the pixels into a single string of values. In one method, the signal at each of the pixels in a column are averaged thus producing a string of m values, one value for each column. FIG. 2A illustrates this process. For example, in the case where the array includes 192 rows, for each image of the laser beam 38 propagating down the optical path 28 is recorded, 192 pixels in a direction perpendicular to the beam direction are averaged. A single value is thereby generated for each column in the detector array that is used to form the image of the laser beam 38 passing through the particle field 10. The string of values produced corresponds to data take for a single optical path 28. As the optical path 28 is traversed through the particle field 10, different images are obtained and thus additional strings of average values are produced. These strings are used to form a representation of the information in the x-y plane. Values for regions between discretely positioned optical paths 28 can be determine by interpolation methods.

Figure 2B:
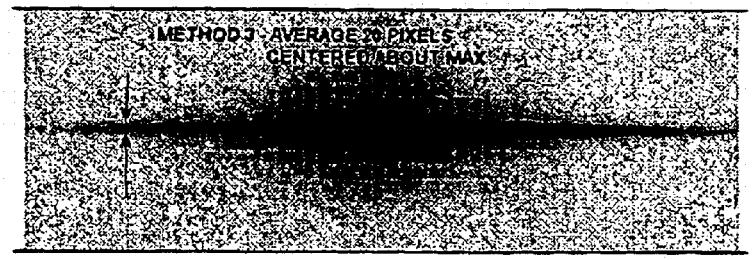

In another method illustrated in FIG. 2B, instead of averaging the entire column, a smaller set of pixels, e.g., 20 pixels total, are considered. The pixel having the largest magnitude within the column is identified. The set of pixels used to form an average is centered about this pixel having the maximum magnitude. In the case where 20 pixels are averaged, 10 are directly above the maximum and 10 are directly beneath the maximum. As described above, this averaging technique when applied across the relevant column is in the detector array produces a string of values as associated with one optical path 28. This method is applied to each image associated with each subsequent optical path 28 used to map out a plane through the particle field. Values for regions between discretely positioned optical paths 28 can be determine by interpolation methods.

Figure 2C:
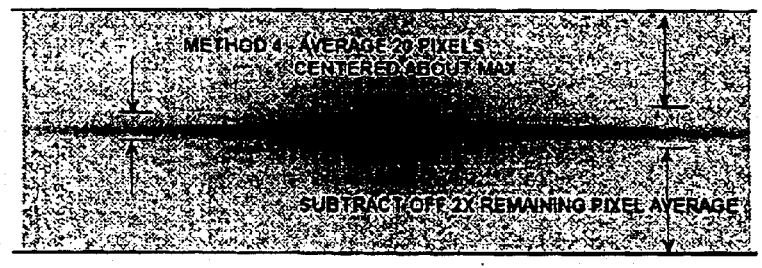

In still another approach, which is depicted in FIG. 2C, in addition to determining the pixel with the maximum mag-

TABLE 1

| Row 1 | Row 2, 3, etc. |
|---|---|
| $\bar{e}_c(x, y_1) = 1$ | $\bar{e}_c(x, y_2) = \exp\left[-\sum_{i=1}^{S} \bar{\xi}_S(\vec{x}_{f,pv} + s_i \hat{n}_{fd}) \Delta s\right]$ |
| $k_S(y_1) = \dfrac{1}{1 - e_{bf_1}} \sum_{i=1}^{N} \tilde{E}'_S(x, y_1) \Delta x$ | $k_S(y_2) = \dfrac{1}{1 - e_{bf_2}} \sum_{i=1}^{N} \tilde{E}'_S(x, y_2)/\bar{e}_c(x, y_2) \Delta x$ |
| $e_b(x, y_1) = 1 - (1/k_S(y_1)) \sum_{1}^{i} (\tilde{E}'_S(x, y_1)) \Delta x$ | $e_b(x, y_2) = 1 - (1/k_S(y_2)) \sum_{1}^{i} (\tilde{E}'_S(x, y_2)) \bar{e}_c(x, y_2) \Delta x$ |
| $\bar{\xi}_S(x, y_1) = \tilde{E}'_S(x, y_1)/k_S(y_1) e_b(x, y_1)$ | $\bar{\xi}_S(x, y_2) = \tilde{E}'_S(x, y_2)/k_S(y_2) e_b(x, y_2) \bar{e}_c(x, y_2)$ |
| $\bar{\xi}_F(x, y_1) = \tilde{E}'_F(x, y_1)/k_F(y_1) e_b(x, y_1)$ | $\bar{\xi}_F(x, y_2) = \tilde{E}'_F(x, y_2)/k_F(y_2) e_b(x, y_2) \bar{e}_c(x, y_2)$ |
| $a(x, y_1) = k_S(y_1) \bar{\xi}_S(x, y_1)$ | $a(x, y_2) = k_S(y_2) \bar{\xi}_S(x, y_1)$ |
| $\rho(x, y_1) = k_F(y_1) \bar{\xi}_F(x, y_1)$ | $\rho(x, y_2) = k_F(y_2) \bar{\xi}_F(x, y_2)$ |

A planar reconstruction from the individual beams can be accomplished in a number of ways. In the case where the nitude in a column and averaging a set of pixels centered about this maximum, an average is computed for the remaining pixels in the column. This later average is subtracted from the average value of the set centered about the maximum. For example, an average of the 20 pixels centered about and slicing through the beam 38 is obtained. In addition, an average of the remaining pixels both above and below the 20 center pixels is determined. Twice the remaining pixel average is subtracted from the 20 pixel average.

In theory, by subtracting out the average of the pixels considered the background, secondary emission can be removed. Any pixel values above or below laser beam 38, which may be about 3–4 millimeters wide (i.e., about 20 pixels) should be caused by secondary emission. Such secondary emission will be generated in the regions both in front of and behind the beam 38 propagating down the optical path 28, as seen by the detectors 22, 24. Thus, this average is doubled before subtracting. This method therefore, provides corrections for secondary emission in the region between the laser beam 38 propagating down the optical path 28 through the particle field 10 and the detectors 22, 24 as well as from behind the laser beam 38.

Figure 2D:
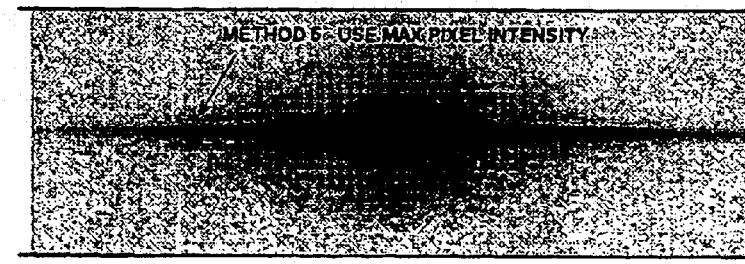

In yet another approach illustrated in FIG. 2D, instead of averaging pixel values in a given column, the maximum pixel magnitude is used. A string of maximum magnitudes values, one for each relevant column, is obtained for each optical path 28. The plane can be reconstructed with a plurality of such strings associated with the different optical paths 28 through the particle field and additional interpolation.

Once the planar information has been constructed, calculations can be performed to convert the raw values of pixel magnitudes into a two-dimensional mapping of the desired information. More specifically, surface area and mass distributions or other properties of interest over a plane within the particle field 10 can be obtained.

The methodology described above for analyzing data obtained by propagating a laser beam 38 over a plurality of paths 28 through the particle field and measuring induced fluorescence and scattering from the individual beams offers several significant advantages. This method enables correction for both laser beam extinction as it passes through the particle field 10 as well as correction for signal attenuation that occurs on the way to the detectors 22, 24. Effects of secondary emission are also reduced by use of a beam of light rather than a sheet. This optical patternation technique is faster and more convenient than mechanical patternation techniques and can utilize a wide variety of optical setups and access such as small windows and maintaining the detector in the plane of interest.

As described above, a single beam 38 can be employed to perform the measurements, although multiple-propagating beams may be used as well. In the multiple beam method, multiple beams 38 propagate down given optical paths 28 which are displaced from each other in the direction out of the x-y plane 44 Traversing single beam(s) 38 reduces secondary emission problems and makes possible a key simplifying feature: light can be collected in the same plane as the traverse or the sheet. Accordingly, the detector 22, 24 can be situated in the plane of the sheet through which the beam is traversed through the particle field 10. As a result, all fluorescence and scattering data, and all the extinction and attenuation effects are measured from within this single plane. A sufficient number of equations can be generated to solve for all the unknowns. Spatial filters 26 at the detectors serve as field stops that masked out a large portion of the secondary emission.

Results

Figure 3:
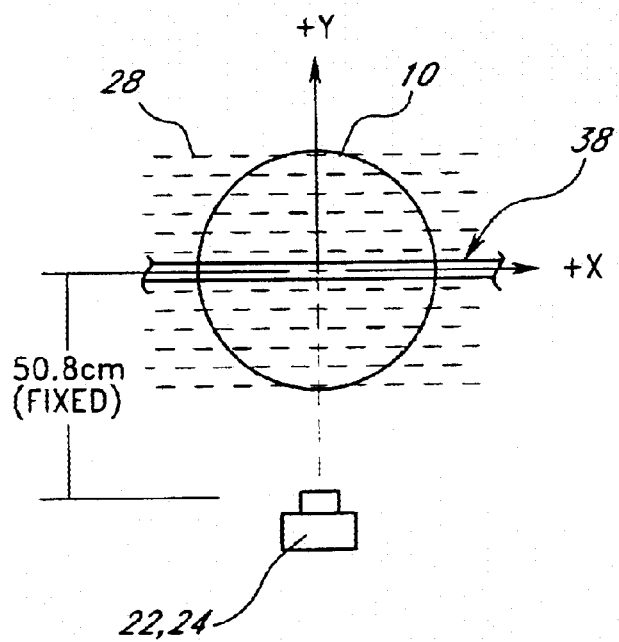
FIG. 3 is a top view that schematically illustrates an embodiment wherein the laser beam held fixed and the particle field is translated through the beam to obtain a plurality of optical paths (represented by dotted lines) that can be used to reconstruct the distributions in the sheet.
Figure 4:
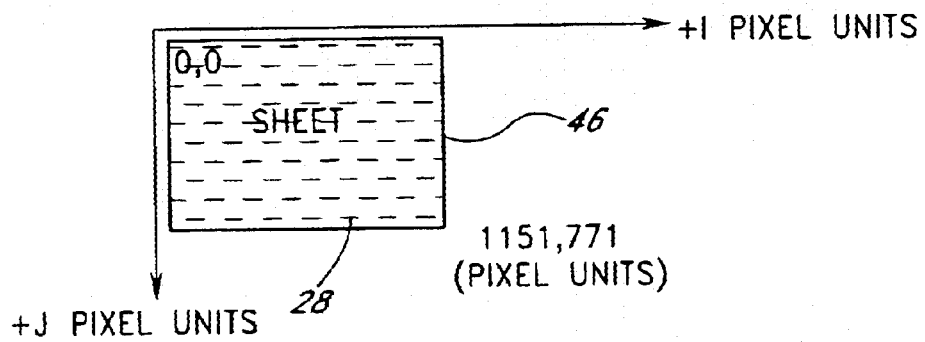
FIG. 4 schematically depicts a rectangular sheet on axes of I and J and in units of pixels showing dotted lines corresponding to a plurality of optical paths used to construct property specific distributions over the sheet.

In one implementation, data are obtained by traversing the particle field away from the detector array, in this example, a two-dimensional detector array. Images of the fluorescence and scatter signals are recorded at simultaneous or subsequent times corresponding to different optical paths 28. The use of single beams 38 in each optical path 28 allows the detector to be placed in the plane of the beam traverse and still obtain information for the entire plane. In this case, the particle field 10 is shifted with respect to the laser beam 38 and the array of detectors in contrast with the apparatus of FIG. 1A, wherein the laser beam is translated by the translator 42. A top view of this configuration with the laser beam 38 held fixed relative to the detector 22, 24 is illustrated in FIG. 3. In this case, the distance between the detector array and the optical path 28 of the laser beam 38 through the particle field 10 is fixed (e.g., in one case at about 50.8 centimeters) while the particle field is translated in a direction parallel to the y-axis. By recording fluorescent and scatter measurements as the particle field 10 is translated, the sheet through the particle field can be mapped out. Such a map 46 on axis of I and J and in units of pixels is shown in FIG. 4. In this example, one pixel corresponds to 0.0091 centimeters; thus, the detector 22, 24 is positioned 5588 pixel units from the laser beam 38. This sheet is constructed from single beams 38, the beams through the most distal portions of the particle field 10 at the I axis (J=0).

FIGS. 5A–5B, 6A–6B, and 7A–7B show results of measurements of the fluorescence and scatter signal, calculations of the excitation beam extinction function (wherein the beam originates from a continuous laser is used and not a pulsed laser) and time averaged signal extinction function based on these measurements, as well as calculations of the surface area concentration distribution and mass or volume concentration distribution. The mass concentration distribution can be converted to a volume concentration distribution and vice versa by knowing the density of the material comprising the particles or droplets in the particle field 10. These images therefore show what the perceived distribution of mass concentration and surface area concentration would be with and without correction for beam extinction and signal attenuation. More specifically, data from the two detectors that receive amounts of scatter and fluorescence, are depicted in FIGS. 5A and 5B, respectively. Two-dimensional plots are mapped out by translating the particle field 10 to obtain a plurality of optical paths 28 within the sheets and interpolating between the optical paths; a cross-section through this 2D plot is shown for each. Images of the laser beam 38 following each optical path 28 were converted into a string of values comprising the maximum signal magnitude as described above with reference to FIG. 2D. In this case, the laser beam 38 propagated from left to right in this plot.

Figure 6A:
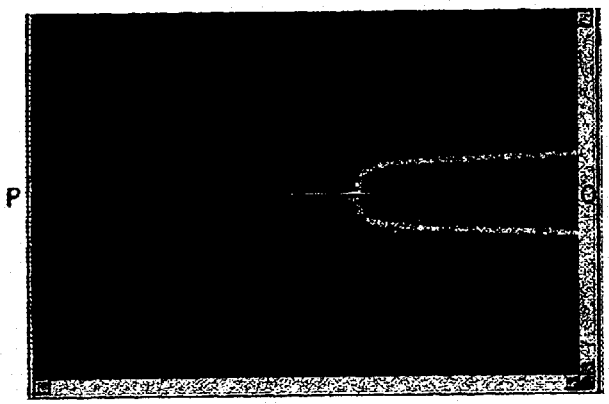
FIGS. 6A and 6B show two-dimensional plots of the calculated time averaged signal attenuation function $\bar{e}_c(x,y)$ and excitation beam extinction function $e_b(x,y)$, respectively, within the sheet as well as a line plot along the line P-Q through the 2D plot.
Figure 6A:
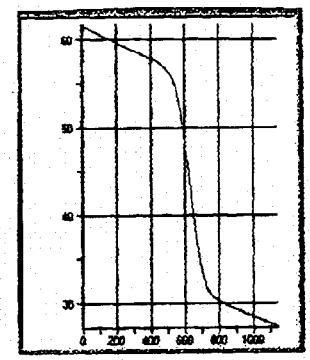
Figure 6B:
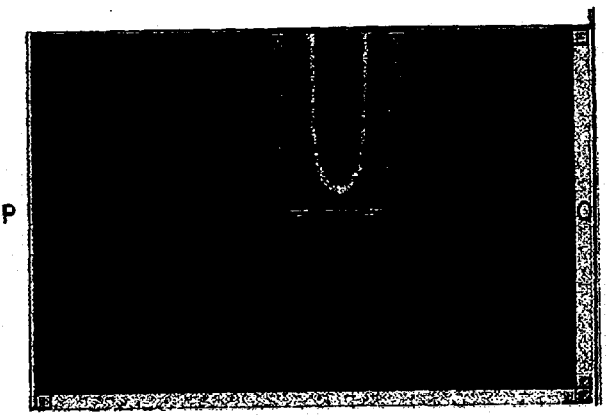
Figure 6B:
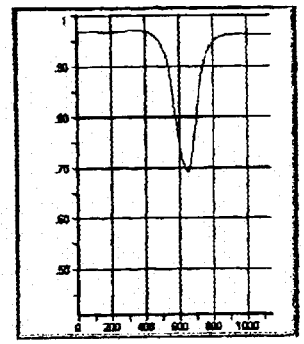

FIG. 6A and 6B presents some of the intermediate quantities computed using the patternation method described above. FIG. 6A show the calculated beam extinction function $e_b(x,y)$ profile within the sheet while FIG. 6B corresponds to the time averaged signal extinction function $\bar{e}_c(x,y)$. As shown, the amount of light is strongly reduced as it propagates through the particle field 10. In particular, the laser power drops from around 61 mW to less than 30 mW along the center of the sheet; see the accompanying cross-section. These results are consistent with the expectations of a "shadow" due to the extinction induced by the spray 10.

The corresponding signal attenuation field $\bar{e}_c(x,y)$, with the position of the detector 22, 24 at the bottom of the plot also shows the presence of strong signal attenuation, with the corrected signal being up to 2.5 times the magnitude of measured signals. Thus, significant corrections were required to overcome the effects of the particulate material between the excitation beam, i.e., the laser beam 28, 38 and the detector 22, 24. The line profile does not intersect the region of minimum attenuation $\bar{e}_c(x,y)$.

Figure 7A:
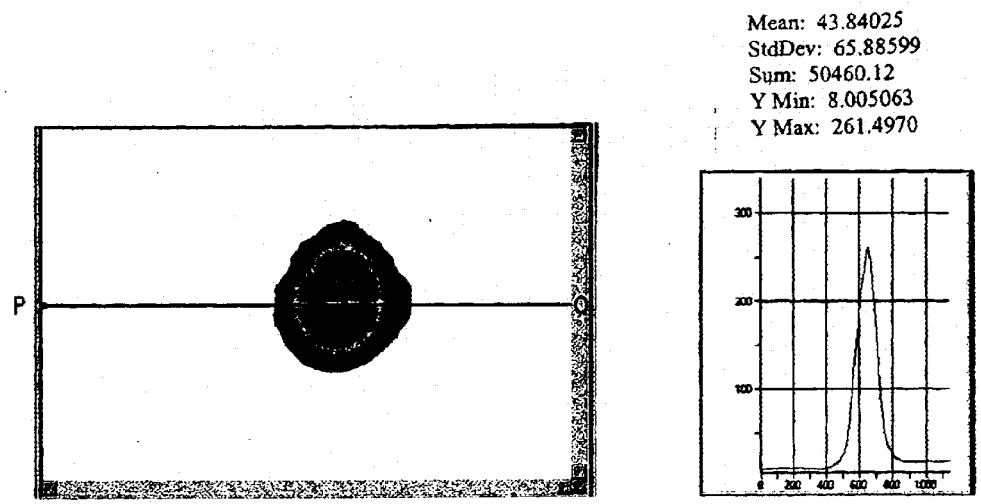
FIGS. 7A and 7B show two-dimensional plots of the corrected area $a(x,y)$ and volume $\rho(x,y)$ distributions, respectively, within the sheet as well as a line plot along the line P-Q through the 2D plot.
Figure 7B:
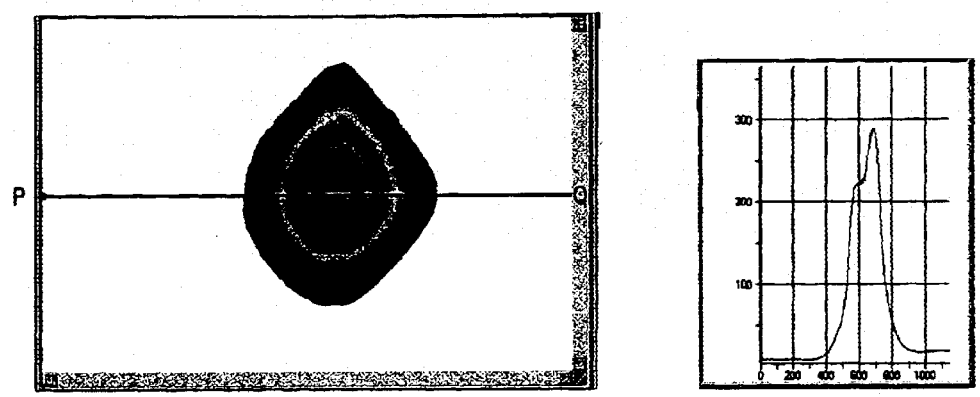

FIGS. 7A and 7B show the corrected surface area and volume distributions, which when compared with the plots in FIGS. 5A and 5B, which are derived by averaging the measured output of the detectors 22, 24, the attenuation and results of correction are clearly illustrated. The corrected volume distribution, shown in FIG. 7B, has a region in the upper right corner of the particle field 10 with maximum mass concentrations. In contrast, the averaged fluorescence signal magnitude from the detector 24, plotted in FIG. 5B, would otherwise indicate that the majority of the mass is located on the left side of the particle field. The effect of attenuation is thus significant enough to warrant correction.

Figure 8:
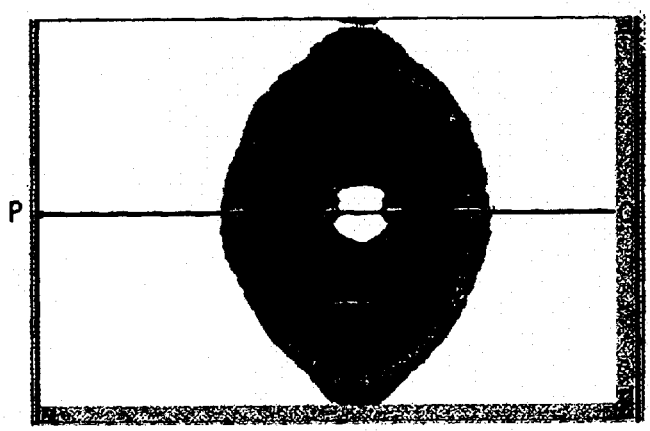
FIG. 8 shows a two-dimensional plot ratio of the corrected fluorescence and scattering signals or equivalently, the ratio of the mass and surface area distributions as well as a line plot along the line P-Q through the 2D plot.
Figure 8:
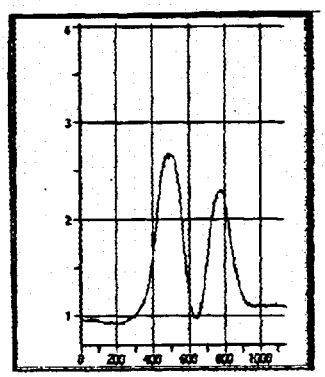

FIG. 8 shows the ratio of the corrected fluorescence and scattering signals or equivalently, the ratio of the volume concentration and surface area concentration distributions. This plot corresponds to a map of the distribution of relative sizes, i.e., Sauter mean diameter (D32) present in the plane of the beam traverse.

It should be noted that all the results presented in FIGS. 5A–5B, 6A–6B, 7A–7B and 8 are "stretched" vertically by about 23%. The aspect ratio can be corrected in these type of measurements by using a calibration grid.

Figure 9A:
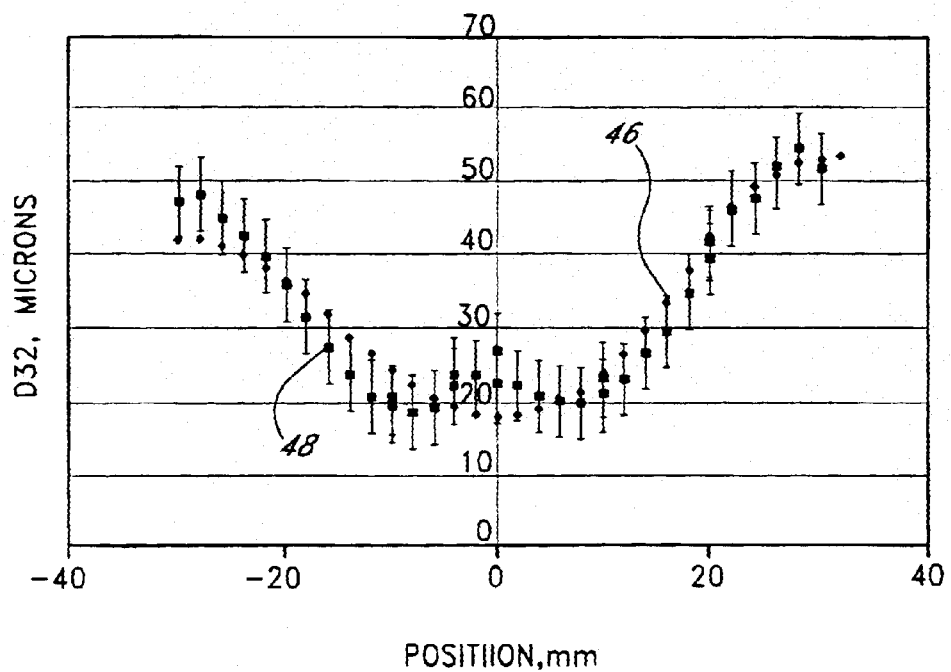
FIGS. 9A and 9B present direct comparisons of measurements of the concentration weighted $D_{32}$ values obtained using phase Doppler interferometry and the apparatus shown in FIG. 1.
Figure 9B:
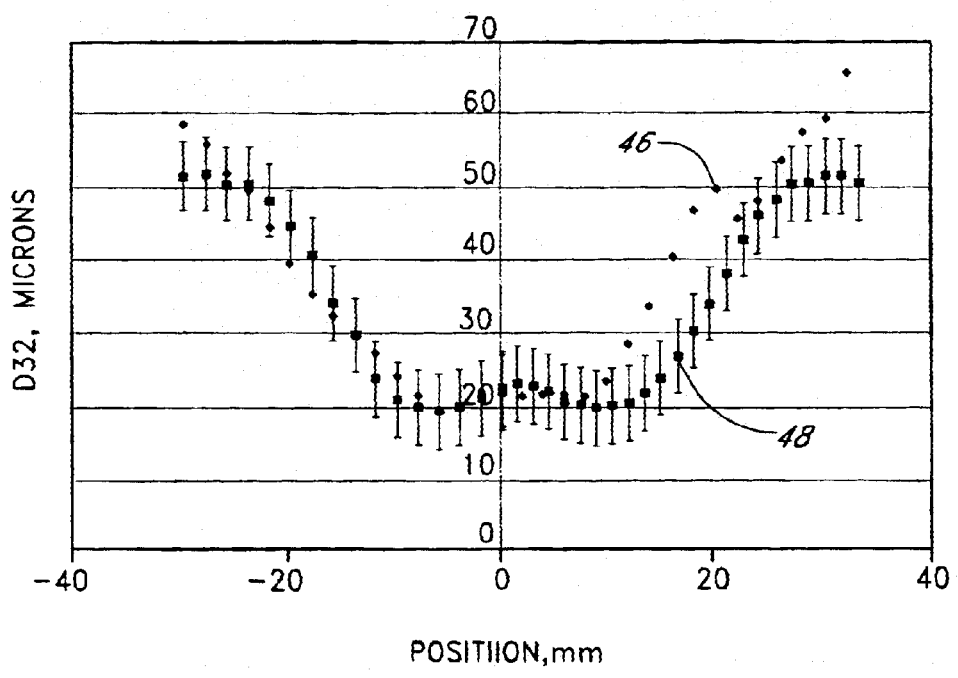

One common technique that can be employed to verify these results is Phase Doppler Interferometer (PDI). Direct comparisons of the values 46 obtained using the method described above with phase Doppler measurements 48 of the concentration weighted $D_{32}$ values are shown in FIGS. 9A and 9B along directions parallel to the x and y axes respectively, i.e., parallel and perpendicular to the excitation beam. A correspondence between the results obtained with PDI and the methodology described above is clear. The PDI measurements 48, however, have limitations. The error bars on the PDI results show expected error based on measurements variation in size at several locations. By varying detector gain and using single vs. two-component operation, variations of 30% could be realized at the centerline and up to 10% at regions near the edge. This variation also leads to problems in establishing a suitable "reference ratio" which is the PDI measured D32 value assigned to a given value of the ratio of the fluorescence signal magnitude to the scattering signal magnitude. In addition, the PDI data 48 suffer from dense particle field effects as well as the uncorrected patternation data. The PDI instrument is a "single particle counter", meaning that it can only measure one particle at a time. In a dense particle field, even the rather small sample volume of the PDI ($200 \times 200$ $\mu m^2$) can possess multiple drops, thereby leading to problems with counting efficiency. The distortion effect discussed above is not found in these plots.

EXAMPLE

Figure 10:
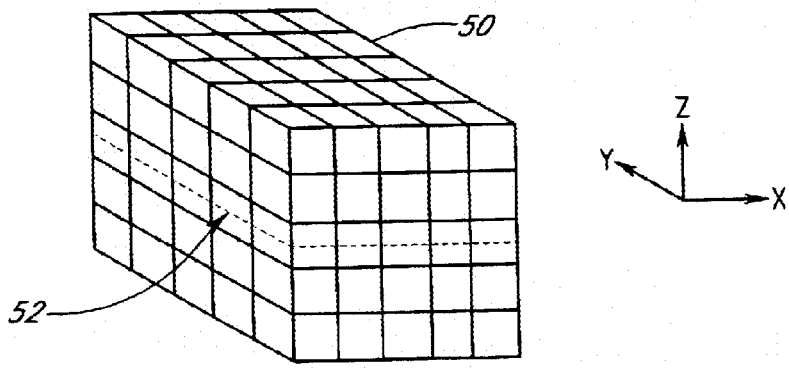
FIG. 10 show a theoretical three-dimensional field having a specific plane of interest passing through the field which can be characterized using the apparatus of FIG. 1.

A simplified example demonstrating the application of this method is presented below. An arbitrary three-dimensional field 50 comprising the region 12 containing, for example, a particle field 10, can be represented in a discretized format as shown in FIG. 10. A specific plane of interest 52 cutting through the field 50 is shown. In this case, for convenience, the plane 52 is parallel to the x-y axes.

Figure 11A:
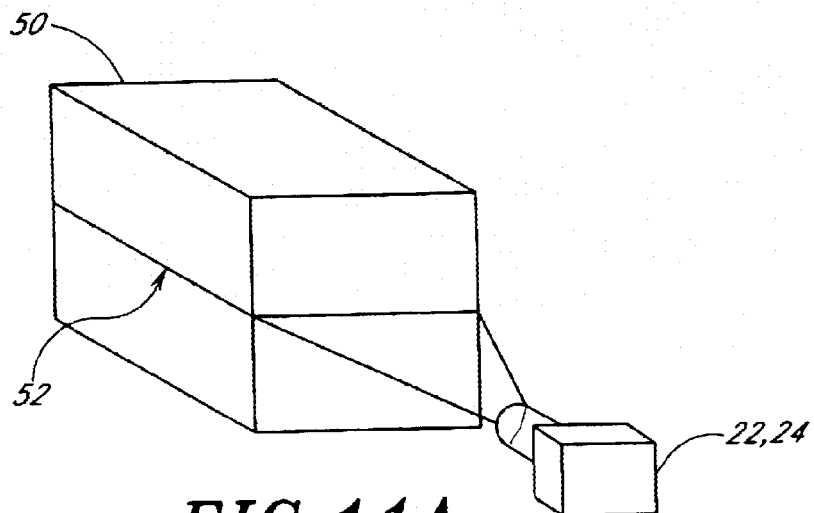
FIGS. 11A and 11B schematically illustrates a detector in the plane of interest for characterizing property-specific distributions in the plane of interest.
Figure 11B:
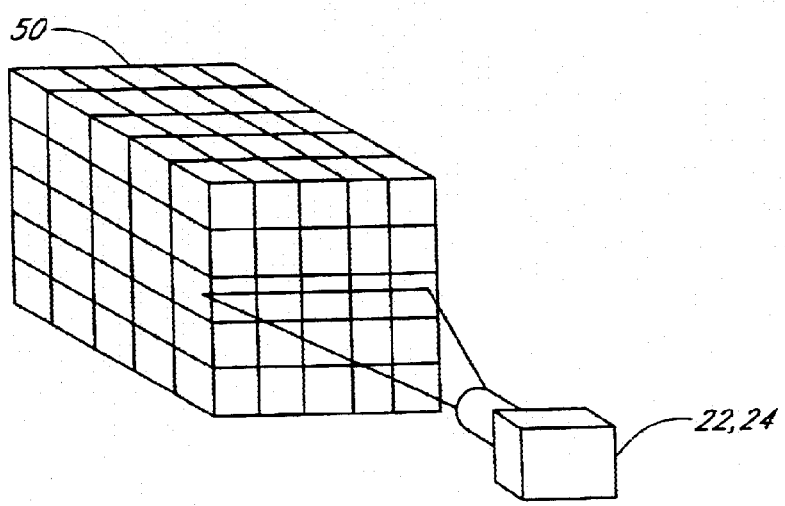

A systematic interrogation of this plane of interest 52 can be executed using a beam of light 38 rather than a sheet and by placing the detector 22, 24 in the same plane as the plane of interest as illustrated in FIGS. 11A and 11B.

Figure 12A:
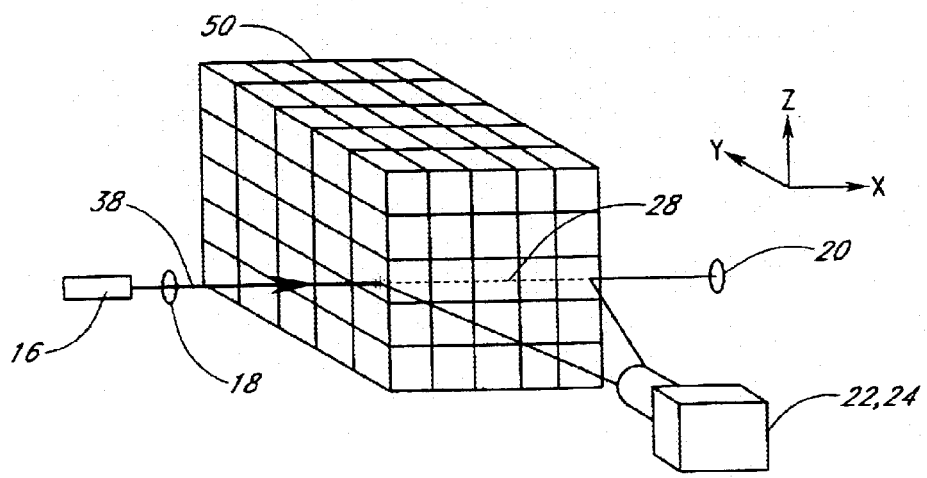
FIGS. 12A–12C depict the laser beam propagating through a series of separate optical paths through the theoretical three-dimensional field to be characterized.
Figure 12B:
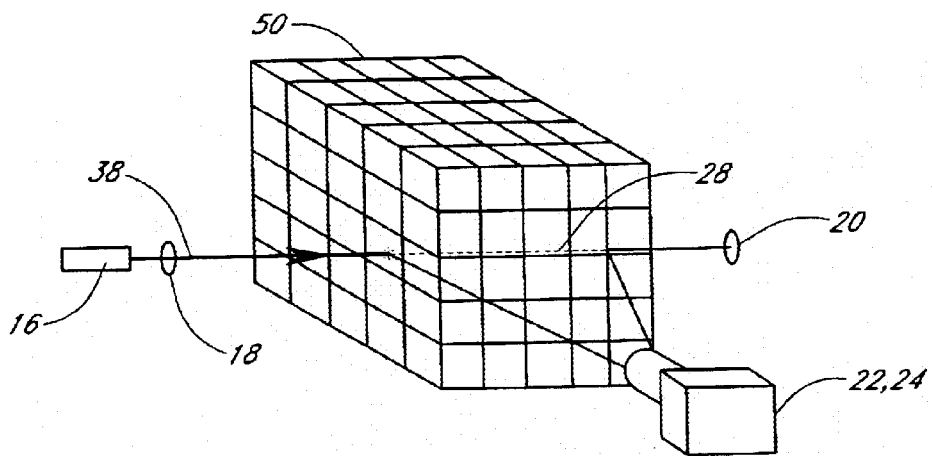
Figure 12C:
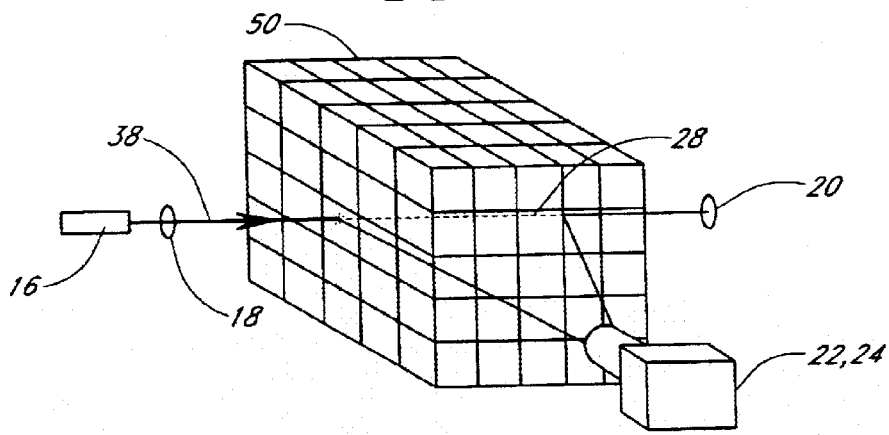

The method described above involves a systematic collection of images of both scattered light and fluorescence. The systematic collection comprises obtaining images at various discrete locations moving into the 3D field 50 as depicted in FIGS. 12A–12C where three of five measurement "stations," referred to above as optical paths 28, are shown. Images obtained for each of the five "stations" will allow the application of the proposed methodology to correct for extinction of the incident beam 38 by the field 28 as well as the attenuation of the signal coming from the measurement station to the detector 22, 24. These data are supplemented with measurements of the amount of light incident on and exiting the field 50. The monitors 18, 20 can be used for this purpose.

Figures 13, 14:
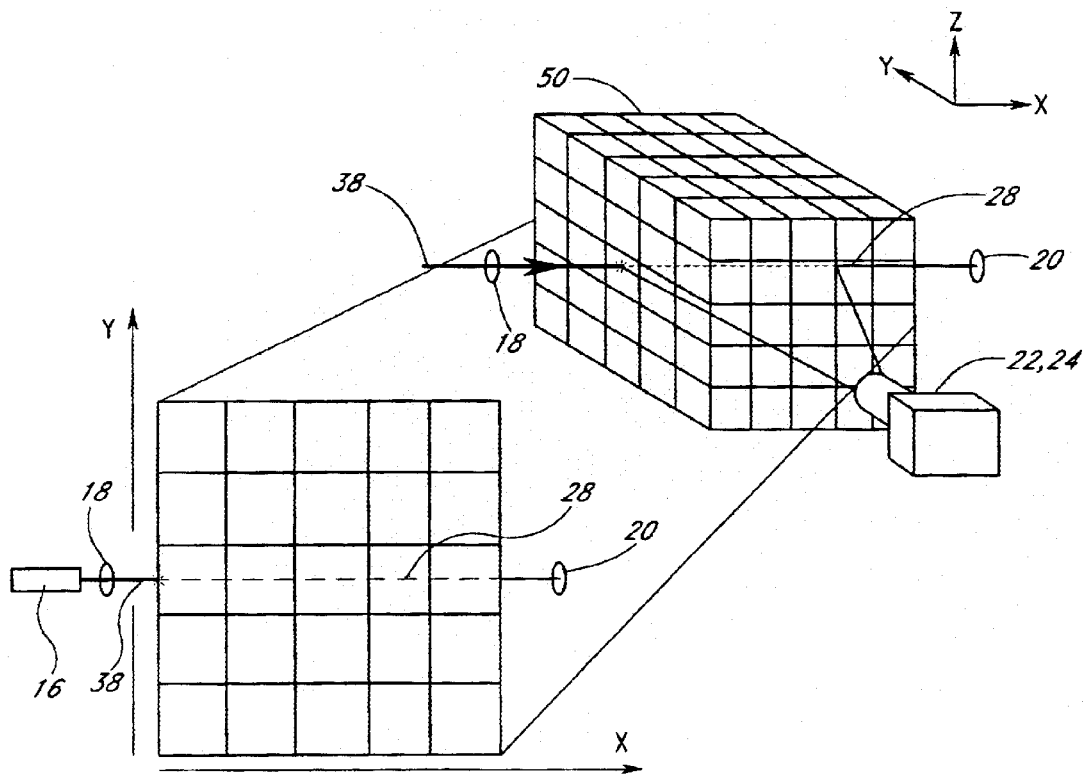
FIG. 13 shows a top view of the plane of interest parallel to the x-y plane at z=3 with a laser beam following an optical path through the field as y=3.
FIG. 14 is a hypothetical 5×5 scattering intensity field $\tilde{E}'_S(x,y)$.

From the results obtained by completing measurements as shown in FIGS. 12A–12C, specific properties within the plane of interest 52 can be characterized and mapped as illustrated by FIG. 13. Maintaining the same discretization scheme, a 5×5 grid is superimposed on this plane of interest 52. The information available by progressing through this plane 52 includes images of the scattered light and of the induced fluorescence from discrete lines corresponding to optical paths 28 of the laser beam 38 through the three-dimensional field 50. In this example, assume that data were acquired at along a five separate paths 28 parallel to the x-axis where y=1, 2, 3, 4, 5. The light beam 38 enters the field 50 at x=0 and exits following the x=5.

Figure 15:
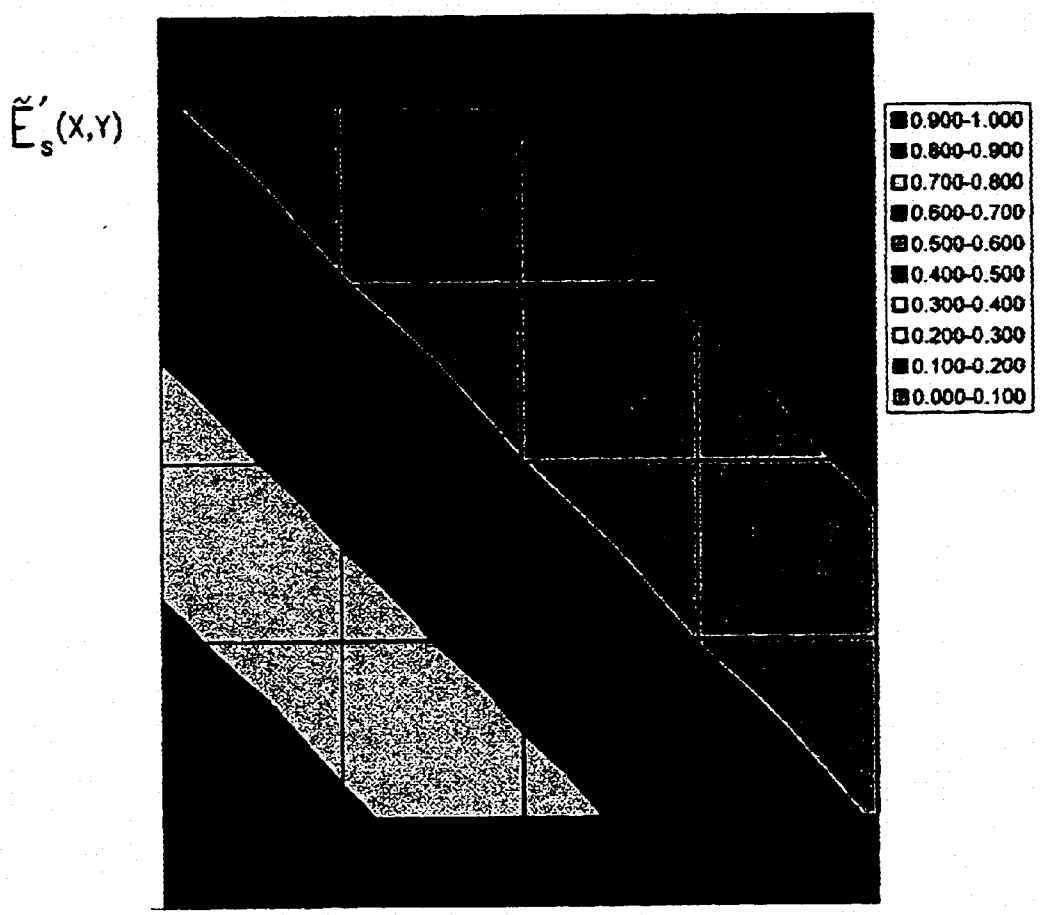
FIG. 15 is a plot of the $\tilde{E}'_S(x,y)$ field shown in FIG. 14.

As a result of assembling the images of the scattering or fluorescence from the light beam 38, a grid of measured signal magnitudes for each in the plane of interest 52 is obtained. Hypothetical values of the detector response, associated with the scattered light, $\tilde{E}'_S(x,y)$ in a 5×5 field representing the plane of interest 52 is shown in FIG. 14. The values contained in each box reflect the measured signal magnitude. Recall that, by definition, the detector response is normalized by the energy per unit time entering the field 50. For convenience, the energy per unit time of the incident light is taken as unity and is noted in the left-most column in FIG. 15. As discussed above, each row corresponding to $y=\{1, 2, 3, 4, 5\}$ is obtained using an independent image of the laser beam 38 as it propagate down a separate optical path 28 as illustrated in FIGS. 12A–12C. A plot of the $\tilde{E}'_S(x,y)$ field is shown in FIG. 15. As described above, the $\tilde{E}'_S(x,y)$ field will not accurately represent the actual surface area because of the extinction of the incident light intensity and the attenuation of the signal exiting the field 50. The first step in providing correction is the application of Equation (10) to determine the constant $k_S$ for the first row (i.e., for y=1). Equation 10 has been rearranged for convenience and discretized as Equation 14

$$k_S(y_1) = \frac{1}{1 - e_{bf_1}} \sum_{i=1}^{N} \tilde{E}'_S(x, y_1) \Delta x, \tag{14a}$$

This equation can be applied to the discretized plane 52 illustrated in FIG. 14 using Equation 14a8.

$$k_s(y_1) = \left(\frac{1}{1 - e_{bf_1}}\right) \sum_{0}^{5} \tilde{E}'_S(x, y_1) \Delta x \tag{14b8}$$

No attenuation of the signal is assumed to occur in the first row (i.e., y=1), thus e(x,1)=1. The values of $E_o(1)$ and $E_f(1)$ are known from the measurements of the power monitors 18, 20 on opposite sides of the field 50; see FIG. 13. For y=1, these values are 1.0 and 0606531, respectively. Also, the $\Delta x$ value is 1 in this example. As a result, $k_S(y_1)$ can be determined for y=1:

$$k_s(y_1) = \left(\frac{1}{1-0.606531}\right)[(0.905^*1) + (0.819^*1) + (0.741^*1) +$$
$$(0.670^*1) + (0.607^*1)]$$
$$= 0.1052$$

With this value of $k_s(y_1)$, the beam extinction function $e_b(x,y_1)$ associated with the first row can be calculated using Equation (12) which has been rearranged and discretized as Equation 15:

$$e_b(x, y_1) = 1 - (1/k_s(y_1))\sum_1^i \left(\tilde{E}'_s(x, y_1)\right)\Delta x, \quad (15)$$

Therefore, for x=1 and y=1, $$e_b(1,y_1)=1-(1/9.5103)\times[(0.905\times1.0)]=0.9048$$

Similarly, $e_b(2,y_1)$ can be obtained.

$$e_b(2,y_1)=1-(1/9.5103)\times[(0.905)\times1.0+(0.819)\times1.0]=0.8187$$

Figure 16:
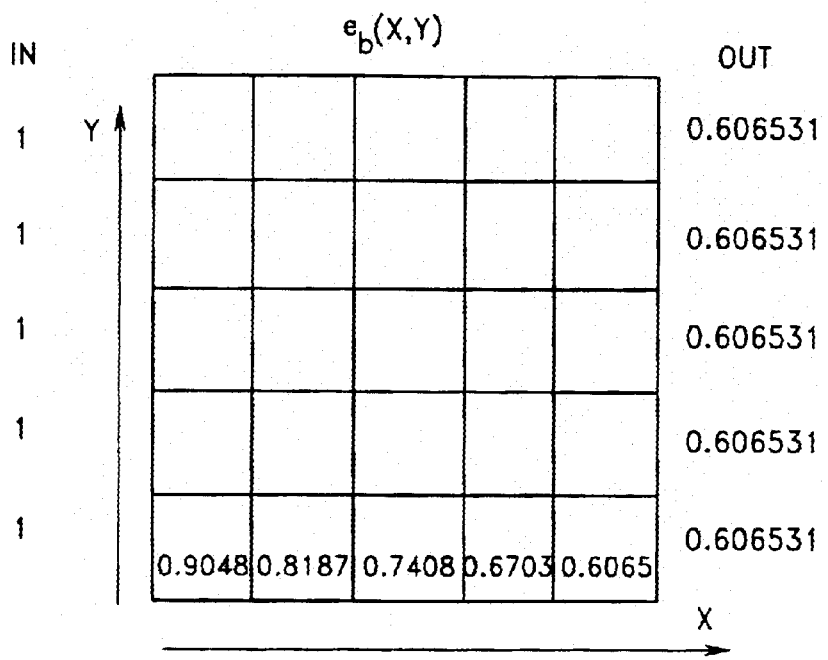
FIG. 16 shows the calculated excitation beam extinction function $e_b(x,y)$ along the first row (y=1)

This process is continued to obtain the value for $e_b(x,1)$. Thus, as by applying Equation (12), the local light extinction function along the first row can be calculated as shown in FIG. 16. Accordingly, the measured $\tilde{E}'_s(x,y)$ combined with the measurement of the total extinction of the beam 38 along the y=1 row allows the laser extinction function at each point to be determined.

Once the local laser extinction function, $e_b(x,y_1)$ and the scattering band coefficient, $k_s(y_1)$, the local elastic scattering band coefficient $\bar{\xi}_s(x,y_1)$ can be determined at each point with Equation (8), which has been rearranged as Equation 16:

$$\bar{\xi}_s(x,y_1)=\tilde{E}'_s(x,y_1)/k_s(y_1)e_b(x,y_1) \quad (16)$$

Hence for x=1, $$\bar{\xi}_s(1, y_1) = \tilde{E}'_s(1, y_1)/k_s(y_1)e_b(1, y_1)$$
$$= 0.905/(9.5103\times0.9048)$$
$$= 0.1052$$

for x=2, $$\bar{\xi}_s(2, y_1) = \tilde{E}'_s(2, y_1)/k_s(y_1)e_b(2, y_1)$$
$$= 0.819/(9.5103\times0.8187)$$
$$= 0.1052$$

The elastic scattering band coefficient $\bar{\xi}_s(x, y_1)$ can be related to the particle surface area in the special case where the particles are spherical and much larger than the wavelength of the light. The expression that relates the surface area to the elastic scattering band coefficient is therefore Equation 17:

$$a(x,y_1)=k_s(y_1)\bar{\xi}_s(x,y_1) \quad (17)$$

For x=1, $$a(1, y_1) = k_s(y_1)\bar{\xi}_s(1, y_1)$$
$$= 9.5103\times0.1052$$
$$= 1.0.$$

For x=2, $$a(2, y_1) = k_s(y_1)\bar{\xi}_s(2, y_1)$$
$$= 9.5103\times0.1052$$
$$= 1.0.$$

Figure 17:
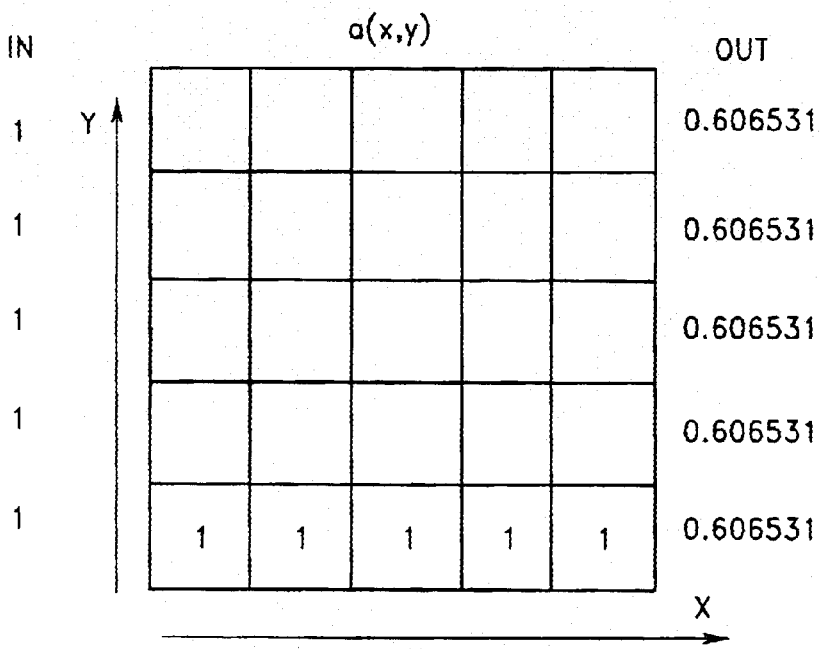
FIG. 17 shows the values of $a(x,y)$, the surface area distribution, calculated for the first row (y=1) of the plane of interest.

The calculated first row values of a(x,y), the surface area distribution, is thus shown by FIG. 17.

The process is continued with calculations for the second row. The image associated this row, i.e., y=2 was obtained by propagation the laser beam 38 down the second optical path 28 as shown in FIG. 12B. At the y=2 position, particles in the particle field 10 are between the light scattering off the field 50 and the detector 22, 24; accordingly the scattering reduces the signal level detected. Equation (11), however, can be applied to correct for this attenuation and has been expressed in discretized form as Equation 18:

$$\bar{e}_c(x, y_2) = \exp\left[-\sum_{i=1}^S \bar{\xi}_s(\vec{x}_{f,pv} + s_i\hat{n}_{fd})\Delta s\right]. \quad (18)$$

Thus for the second row, the process applied to the first row is repeated, with values of $e_c(x,2)$ being calculated as well. Pursuant to this model, $e_c(1,2)$ can be determined from the value of $\bar{\xi}_s(1,y_1)$, which is equal to 0.1052.

Note that, for this example, the detector is assumed to be infinitely far from the three-dimensional field 50 under test. As a result, the direction cosines defined reduce to 1. Further, for simplicity, it is assumed that the rays from the second row only interact with the material in the same column of the first row. As a result, only a(1,1) enters into the exponential. Additionally, $\Delta y$ is taken as equal to $\Delta x$, namely 1.0; hence $\Delta s=1.0$. Thus, for this example:

$$e_c(1,2)=\exp-[0.1052\times1.0]=0.9002$$

Figure 18:
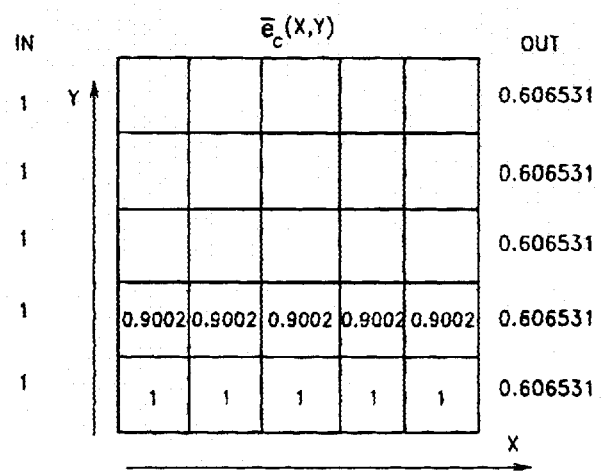
FIG. 18 depicts the calculated time averaged signal attenuation function $\bar{e}_c(x,y)$ for the first two rows, $\bar{e}_c(x,1)$ being assumed to be equal to unity.

The same strategy is applied to all x values for $e_c(x,2)$. In this simplified example, since a(x,1)=1.0 everywhere, $e_c(x,2)$ is the same for all x. The resultant $e_c(x,y)$ field is shown in FIG. 18.

With the $e_c(x,2)$ values available, $k_s$ for the second row can be calculated using Equation (7). In this case, the attenuation values $e_c(x,2)$ are 0.9002.

$$k_s(y_2) = \frac{1}{1-0.606531}\left[\frac{0.815}{0.9002}\times 1 + \frac{0.737}{0.9002}\times 1 + \frac{0.667}{0.9002}\times 1 + \frac{0.603}{0.9002}\times 1 + \frac{0.546}{0.9002}\times 1\right]$$

$$= 9.513$$

With this value of $k_S$ for the second row, Equation (15) can then be applied to determine the laser extinction $e_b(x,y_2)$ at each point along the second row.

$$e_b(x, y_2) = 1 - (1/k_s(y_2))\sum_1^i (\tilde{E}'_s(x, y_2)/\bar{e}_c(x, y_2))\Delta x$$

$$e_b(1, y_2) = 1 - (1/9.5103)\times[(0.815/0.9002)\times 1.0]$$
$$= 0.9408$$

Similarly, $e_b(2,y_2)$ can be obtained, $$e_b(1,y_2)=1-(1/9.5103)\times[(0.815/0.9002)\times 1.0 + (0.737/0.9002)\times 1.0] = 0.8187$$

Figure 19:
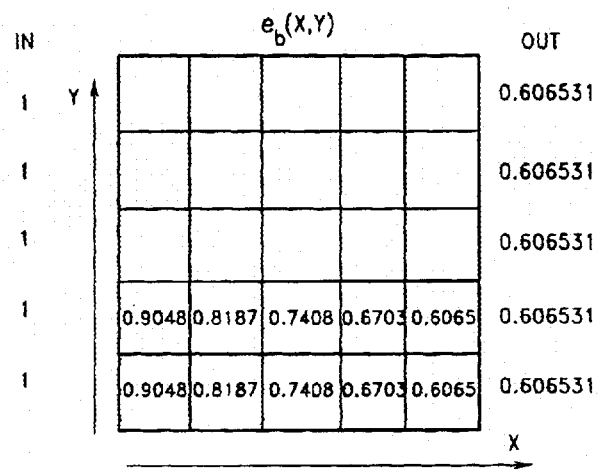
FIG. 19 shows the calculated excitation beam extinction function $e_b(x,y)$ for the second row, y=2.

The remaining values of the beam extinction function in this row can similarly be computed. FIG. 19 displays the calculated beam extinction function values for the second row. They are identical to the first row because the model $a(x,y)$ field selected for in this example.

Knowing $k_S(y_2)$ and $e_b(x, y_2)$ and $e_c(x,y_2)$, the elastic scattering band coefficients $\bar{\xi}_S(x, y_2)$ can be determined along the second row:

$$\bar{\xi}_S(x,y_2)=\tilde{E}'_s(x,y_2)/k_S(y_2)e_b(x,y_2)\bar{e}_c(x,y_2)$$

Hence, for x=1, $$\bar{\xi}_S(1,y_2)=\tilde{E}'_s(1,y_2)/k_S(y_2)e_b(1,y_2)\bar{e}_c(1,y_2)$$

$$\bar{\xi}_S(1,y_2)=0.815/(9.5103\times 0.9048\times 0.9002)=0.1052$$

The elastic scattering band coefficients $\bar{\xi}_S(1,y_2)$ can be used to determine the surface area values, $a(1,y_2)$, at those points, $$a(1,y_2)=k_S(y_2)\bar{\xi}_S(1,y_2)$$

$$a(1,y_2)=9.5103\times 0.1052=1.0$$

Figure 20:
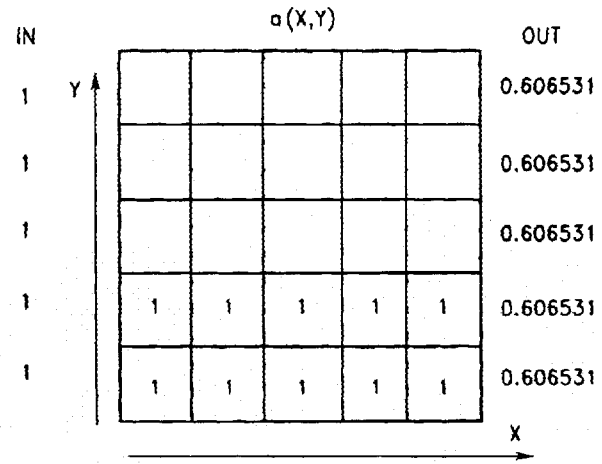
FIG. 20 depicts the surface area distribution $a(x,y)$ calculated for the first two rows.

The resulting values of $a(x,y)$ for rows 1 and 2 are summarized in FIG. 20.

Figure 21:
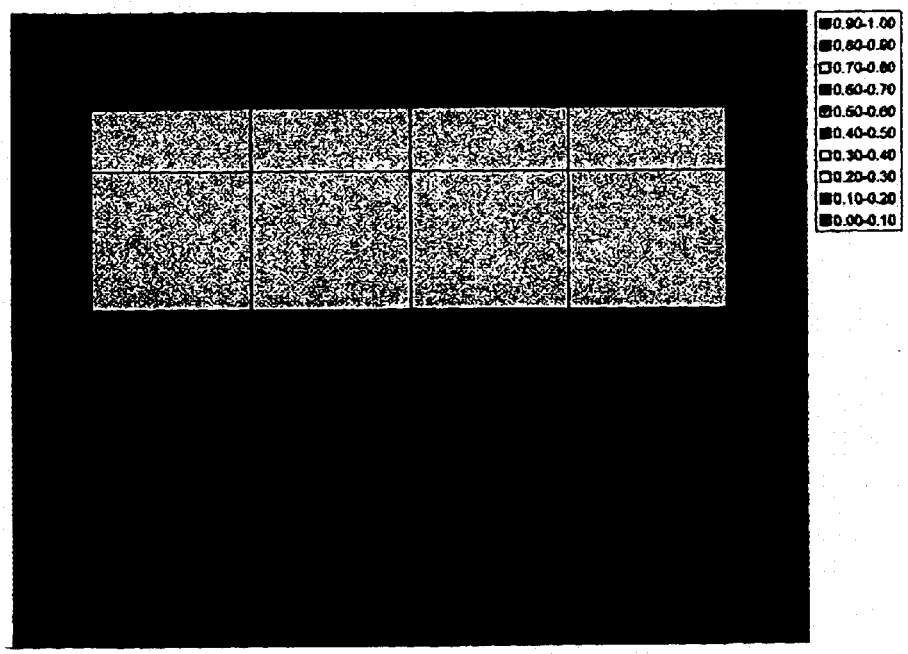
FIG. 21 shows surface area distribution without using correction.

This process continues for each subsequent row, y=3, 4, and 5. The values for $e_c(x,y)$ decrease as the attenuation of the signal increases. Accordingly, the $e_c(x,y)$ field can be utilized to account for attenuation of the signal; else the surface area distribution would be skewed. FIG. 21 illustrates the perceived surface area distribution if the extinction of the incident light was accounted for, but the signal attenuation was not accounted for. As shown, the surface area at the top of the image is 60% of the values at the bottom as a result of the attenuation of the signal from the top side. The portion of the field 50 between the top row (or far row) and the detector attenuates the signal.

Figure 22:
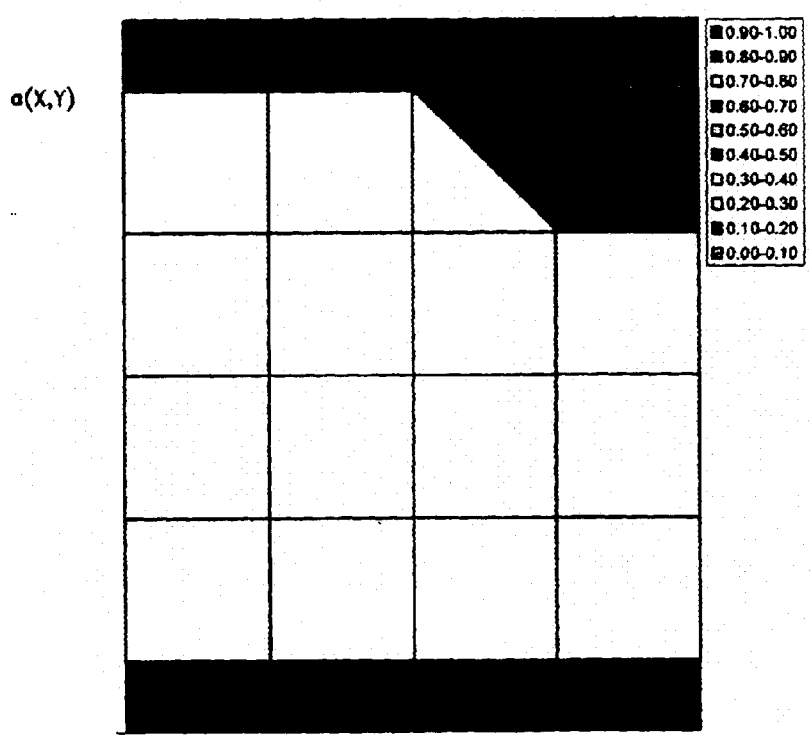
FIG. 22 shows the corrected surface area distribution $a(x,y)$.

If the $e_c(x,y)$ field is utilized to account for the attenuation of the signal light for the field shown in FIG. 21, then the result shown in FIG. 22 is generated, correctly corresponding to the uniform field expected. As shown in FIG. 15, in the absence of corrections to account for attenuation of the incident laser light and the signal light exiting the field 50, the perceived and actual surface area distributions are significantly different.

The same principles described above apply to the fluorescence field $\tilde{E}'_F(x,y)$, where the same corrections for the laser intensity extinction and signal attenuation can be applied. In the case of fluorescence, Equation (9) applies instead of Equation (8). And in this case, the images obtained would be of the fluorescence rather than of the scattering (i.e., $\tilde{E}'_F(x,y)$ instead of $\tilde{E}'_S(x,y)$). Note that the values of $e_b(x,y)$ as calculated in the illustration above are exactly the same for the fluorescence and scattering. As a result, the extinction functions are knows throughout the field and $\tilde{E}'_F(x,y)$ can be calculated for any given x,y without adhering to a strict order (i.e., the requirement to step through the field in a specific order is not required). $k_S$ is again utilized because it is assumed that scattering is the dominant means of extinction for both the elastically scattered light and the fluorescence. The constant $k_F$ however, is not obtained explicitly. As a result, the mass concentration is only known to within a constant made up of the product of $k_F$ and another constant that relates the fluorescence band cross-section to the mass concentration.

It is also noted that, for the case of fluorescence, $\bar{\xi}_F$ may vary over time. Possible reasons include, but are not limited to, changing batches of liquid, or in the case of a dye, changes in the dye concentration or emission quantum efficiency. By monitoring emission from a sample of the liquid, for example running through a flow cell, this effect can be accounted for through a term that adjusts $\tilde{E}'_F(x,y)$ accordingly. The signal from the monitor will provide a value of the emission characteristic of the liquid against which $\tilde{E}'_F(x,y)$ can be normalized. If the value of the emission characteristic changes, $\tilde{E}'_F(x,y)$ will be adjusted accordingly.

Figure 23:
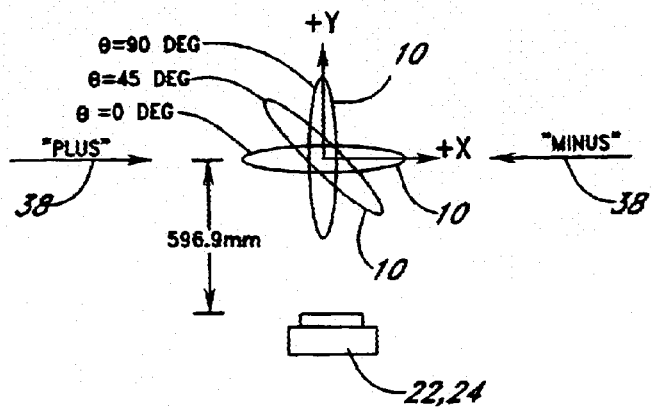
FIG. 23 is a schematic drawing illustrating various orientations of the fan spray used in validation experiments.
Figure 24:
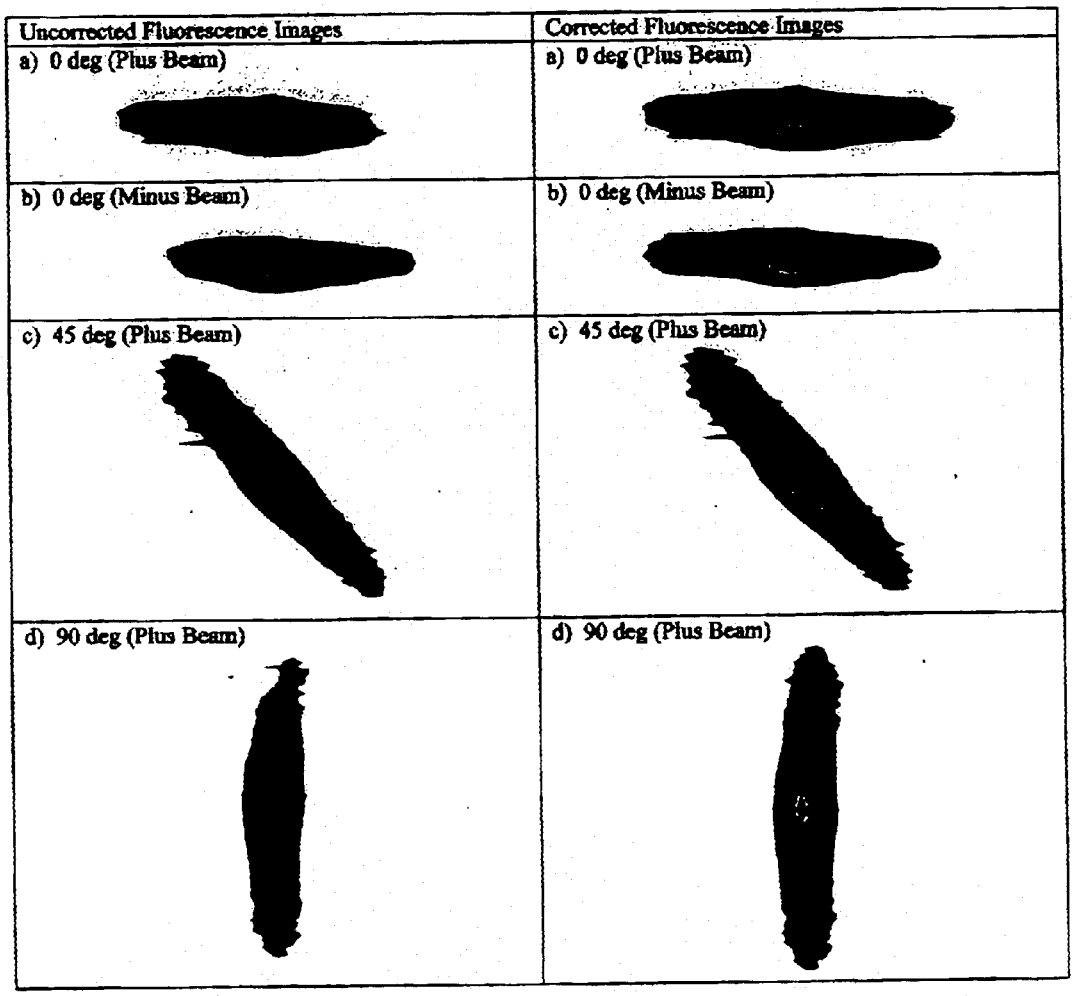
FIGS. 24A–24D are plots of uncorrected and corrected particle field volume distributions.
Figure 25B:
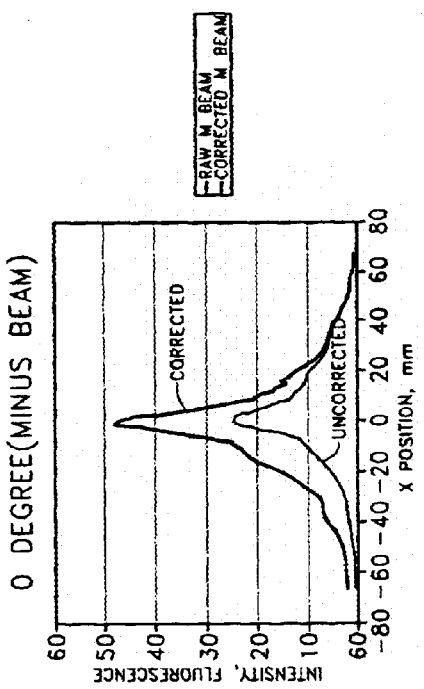
FIG. 25 are plots on axes of fluorescence (in arbitrary units) versus position (in millimeter) of comparing uncorrected fluorescence with corrected volume distributions.
Figure 25D:
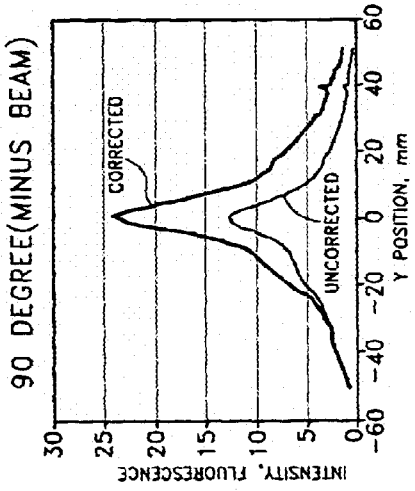
Figure 25A:
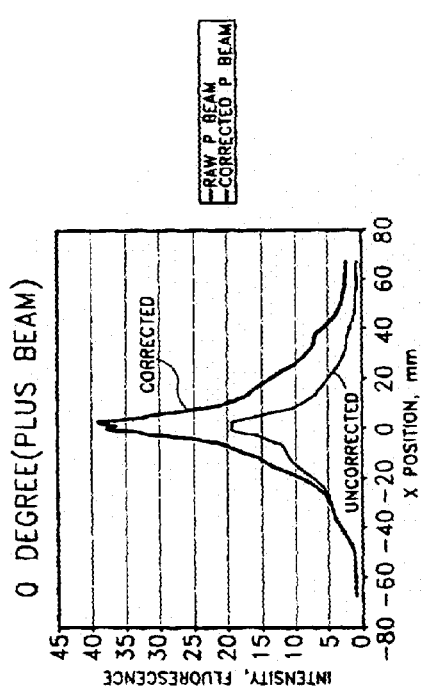
Figure 25C:
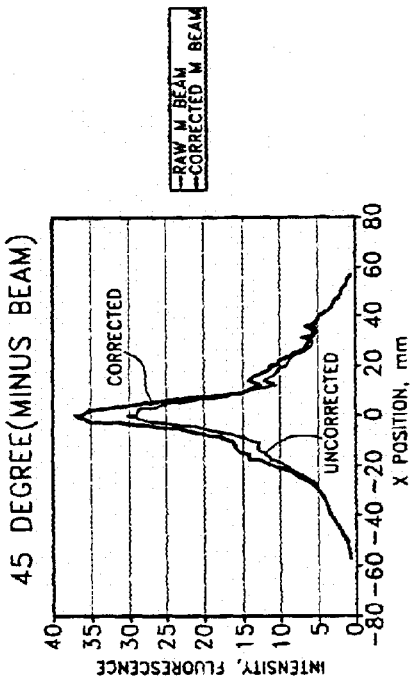
Figure 26:
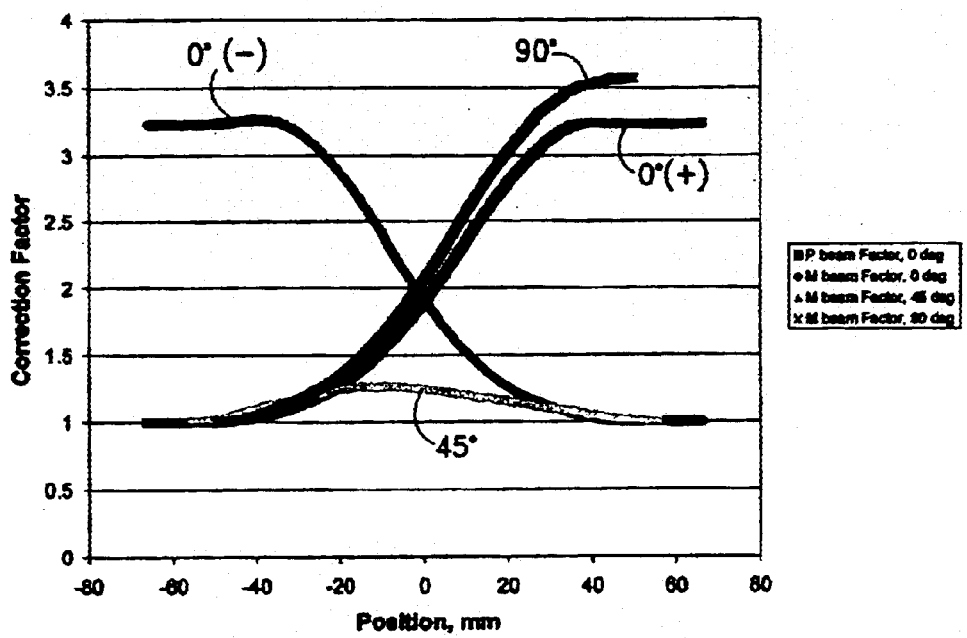
FIG. 26 are plots on axes of correction factor (in arbitrary units) versus position (in millimeter) of the ratio of line profiles of corrected to uncorrected volume distributions.
Figure 27:
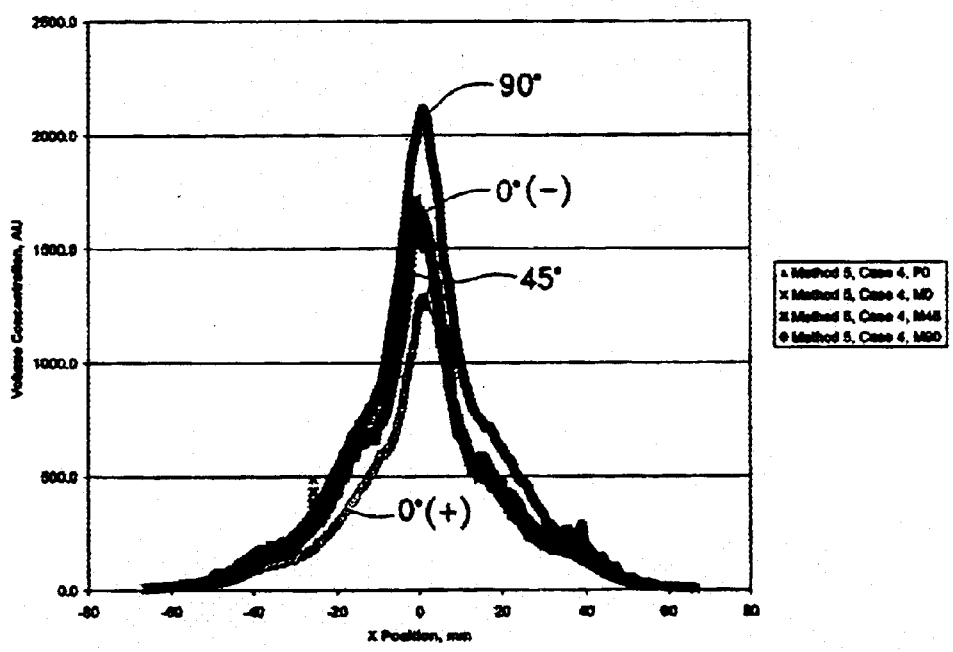
FIG. 27 are line plots on axes of volume concentration (in arbitrary units) versus position x (in millimeter) for the four differently directed laser beams 0° (+x), 0° (−x), 45°, and 90°.

To further validate the principle, an additional set of test data were obtained using a fan spray. The fan spray could be selectively oriented to produce either (1) large extinction of the incident light, (2) large attenuation of the signal light, or (3) little effect on either. FIG. 23 illustrates the orientations. A 0° orientation, parallel to the laser beam 38 propagating down the optical path 28, leads to maximum attenuation of the incident light, the 90° orientation, perpendicular to the propagation of the laser beam results in maximum attenuation of the signal light, and the 45° orientation results in only moderate attenuation of both the excitation light and the output signal. Note that data were obtained in the 0° orientation for a beam traversing from either direction from left to right and from right to left, herein denoted the plus and minus beams to coincide with the +x and −x directions. Also note that, in no case was the "PLUS" beam 38 and "MINUS" beam 38 illuminating the field 10 simultaneously. Rather, for the 0 DEG orientation, images were obtained for with the "PLUS" beam 38 illumination and subsequently with the "MINUS" beam 38 illumination. In this case the detector 22, 24 contained a 576×192 detector array. Calculations were performed by computer to analysis and to correct the measurements. FIG. 24A–24D show surface relief plots of the uncorrected and corrected particle field volume distributions. FIG. 25A–25D present line profiles taken from the images of the scattered light and comparing the uncorrected and corrected profiles for each orientation and beam direction. The difference between the two lines for each plot reflects the extent to which the extinction of incident light and/or attenuation of the signal light affects the perceived surface area. To further illustrate the magnitude of the differences, the ratio of the corrected to uncorrected profiles are shown in FIG. 26. The results show that, for the spray studied, failure to account for attenuation mechanisms, the volume concentration will be underestimated by a factor of greater than three in some parts of the spray. FIG. 27 presents a direct comparison of the corrected volume distributions obtained for the differently directed laser beams 38. Although the shapes are fairly similar, the magnitudes vary some. There are several possible reasons for this, which include the possibility that the nozzle is angled relative to the coordinate system associated with the traversing and that the nozzle is not rotating about its centerline. Also for the 0° plus and minus case, two different laser beams are utilized with slightly different physical diameters although the total intensity of the two beams was maintained within 3%. In addition, although ideally the beams are aligned on a common axis, one may have been slight displaced with respect to the other. As a result, it is possible that the line profiles extracted were not exactly aligned with the same exact part of the spray.

To explore this possibility, a crude error estimation was done by looking at the actual values in the neighborhood of the 0 position. Due to the optical setup utilized, 1 mm is equivalent to 13 pixels. It was assumed that the rotation of the nozzle about its centerline could not be ensured to any greater precision (indeed, it is likely that the positioning uncertainty is even greater). Upon comparison of the centerline values shown in FIG. 27 to those found +/−1 mm in the Y direction and +/−0.5 mm in the X direction, variation in the peak values of +/−300 was observed. As a result, an uncertainty in the peak values shown in of +/−300 should be considered in the comparison of the results for the different nozzle orientations. If this uncertainty is considered, then the peak values from each of the orientations is the same within experimental uncertainty.

Figure 28:
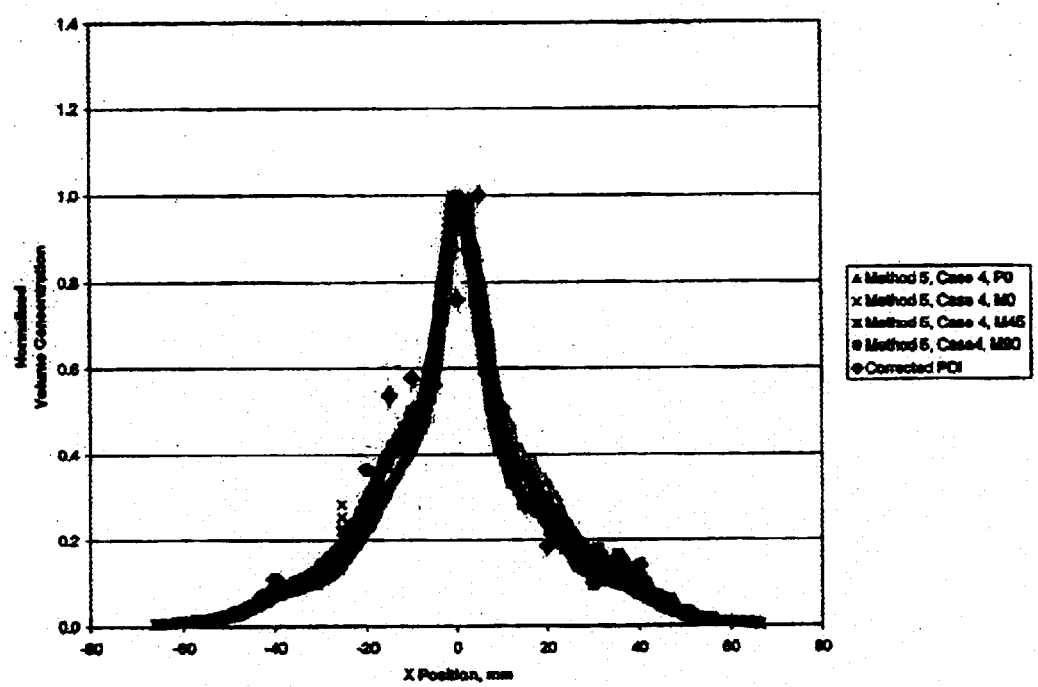
FIG. 28 line plots on axes of normalized volume concentration (in arbitrary units) versus position x (in millimeter) comprising of measured volume concentration for the four differently directed laser beams 0° (+x), 0° (−x), 45°, and 90° with measurements obtained by Phase Doppler Interferometry (PDI).

Finally, FIG. 28 compares the four profiles with an independent measurement of the volume concentration using phase Doppler interferometry.

The methods described above can be practiced in many forms by a variety of apparatus. For example, systems that simultaneously provide multiple probe beams such as, e.g., Gaussian beams or beams having a circularly symmetric cross-section, can be employed to expedite data acquisition. These beams can be oriented in substantially similar directions. Preferably, however, a single beam is used to sample the particle field to minimize secondary emission. Preferably, this beam is a collimated beam and is small in size and may comprise, for example, a Gaussian beam or a beam having a circularly symmetric cross-section. This beam may be produced by a laser or by other light sources which preferably are spectrally coherent and tuned to the appropriate wavelength to interact with the particle field and to produce the desired output signals. Preferably, the beam includes light having a single polarization state but the method is not so limited. The detectors may also comprise a variety of devices that are sensitive to the optical signals produced when the probe beam is passed through the particle field. Spectral filters may be included to filter out undesirable wavelengths accompanying the optical signals. Similarly, a mask, spatial filter, or field stop may be employed to remove background light, e.g., light originating from portions of particle field not within the optical path of the probe beam or portions of the optical path not being measured. A flow cell, a chamber for containing a portion of the particle field or a smaller volume of particles as in the particle field and that allows optical access to a probe beam and to an optical sensor can be included to monitor the fluorescence properties of the particles. The probe beam would induce fluorescence in the particles within the chamber and the optical sensor would detect the resultant fluorescence. If the fluorescence properties fluctuate, these variations can be considered in calculating the desired property specific distributions. Other arrangements that allow the fluorescence properties of a small volume of the particles to be monitored are also considered possible. The methods above can also be employed under certain circumstances to characterize property-specific distributions of spherical and/or non-spherical particles.

Although the foregoing description of the preferred embodiments of the present invention has shown, described and pointed out the fundamental novel features of the invention, it will be understood that various omissions, substitutions, and changes in the form of the detail of the apparatus as illustrated as well as the uses thereof, may be made by those skilled in the art, without departing from the spirit of the invention.

What is claimed is:

1. A method of determining mass distribution within an ensemble of particles, comprising:
   directing a beam of excitation light into the ensemble, the beam propagating along an optical path within the ensemble;
   generating laser induced fluorescence (LIF) from particles along the optical path with the excitation light, the particles scattering and thereby attenuating the excitation light propagating along the optical path;
   comparing the amount of light exiting the ensemble against the amount of light entering the ensemble to determine the extent to which the excitation light is attenuated by the ensemble;
   detecting LIF originating from various points along the optical path with a detector to generate respective LIF signals;
   detecting scattered excitation light originating from various points along the optical path with a detector to generate respective scattered excitation light signals, wherein the scattered excitation light undergoes additional scattering as it propagates away from the optical path and towards the detector used to detect scattered excitation light; and
   computing the mass distribution of the particles along the optical path using said LIF signals and said scattered excitation light signals, while accounting for the attenuation of the excitation light propagating along the optical path and while accounting for said additional scattering of the scattered excitation light.

2. The method of claim 1, comprising repeating said method for different optical paths to generate a mass distribution of the ensemble.

3. The method of claim 2, wherein the mass distribution of the ensemble is calculated by first analyzing LIF signals and scattered excitation light signals corresponding to a baseline optical path for which said additional scattering of the scattered excitation light is negligible, and then analyzing LIF signals and scattered excitation light signals corresponding to optical paths adjacent the baseline optical path in an iterative fashion, such that said additional scattering of the scattered excitation light incrementally increases with each subsequently analyzed optical path.

4. The method of claim 1, wherein the LIF undergoes scattering as it propagates away from the optical path and towards the detector used to detect LIF, the method further comprising accounting for said LIF scattering to more accurately calculate the mass distribution of the particles along the optical path.

5. The method of claim 1, wherein the beam of excitation light is a planar sheet of laser light.

6. The method of claim 1, wherein the beam of excitation light is a laser beam.

7. The method of claim 1, wherein the same detector is used to generate the LIF signals and the scattered excitation light signals.

8. The method of claim 7, wherein a filter is used to distinguish light at the excitation and LIF wavelengths.

9. The method of claim 1, wherein said determining the extent to which the excitation light is attenuated by the ensemble comprises monitoring the intensity of the excitation light entering the ensemble.

10. The method of claim 1, further comprising computing the surface area distribution.

11. The method of claim 10, wherein the surface area distribution is computed from the scattered excitation light signals and the extent to which the excitation light is attenuated by the ensemble.

12. A method of determining mass distribution within an ensemble of particles, comprising:
    performing a procedure for determining the mass distribution of particles within a region of the ensemble, including:
        directing a single collimated beam of excitation light into the ensemble, the beam propagating along a first optical path within the ensemble;
        generating laser induced fluorescence (LIF) from particles along the optical path with the excitation light, the particles scattering and thereby attenuating the excitation light propagating along the optical path;
        comparing the intensity of the excitation light exiting the ensemble against the intensity of the excitation light entering the ensemble to determine the extent to which the excitation light is attenuated by the ensemble;
        detecting LIF originating from various points along the optical path with a detector to generate respective LIF signals;
        detecting scattered excitation light originating from various points along the optical path with a detector to generate respective scattered excitation light signals; and
        computing the mass distribution of the particles along the optical path using said LIF signals and said scattered excitation light signals while accounting for the attenuation of the excitation light propagating along the optical path; and
    repeating said procedure for a different region of the ensemble by directing the beam along a second optical path different from the first optical path, wherein the first and second optical paths lie in a common plane and correspond to adjacent regions of the ensemble.

13. The method of claim 12, comprising repeating said procedure to generate a mass distribution of the ensemble.

14. The method of claim 12, wherein the scattered excitation light undergoes additional scattering as it propagates away from at least one of the optical paths and towards the detector used to detect scattered excitation light, the method further comprising accounting for said additional scattering when calculating the mass distribution of the particles along said at least one of the optical paths.

15. The method of claim 14, wherein the mass distribution of the ensemble is calculated by first analyzing LIF signals and scattered excitation light signals corresponding to a baseline optical path for which said additional scattering of the scattered excitation light is negligible, and then analyzing LIF signals and scattered excitation light signals corresponding to optical paths adjacent the baseline optical path in an iterative fashion, such that said additional scattering of the scattered excitation light incrementally increases with each subsequently analyzed optical path.

16. The method of claim 14, wherein LIF undergoes scattering as it propagates away from at least one of the optical paths and towards the detector used to detect LIF, the method further comprising accounting for said LIF scattering to more accurately calculate the mass distribution of the particles along said at least one of the optical paths.

17. The method of claim 12, wherein the beam of excitation light is a laser beam.

18. The method of claim 12, wherein LIF undergoes scattering as it propagates away from at least one of the optical paths and towards the detector used to detect LIF, the method further comprising accounting for said LIF scattering to more accurately calculate the mass distribution of the particles along said at least one of the optical paths.

19. The method of claim 12, wherein the same detector is used to generate the LIF signals and the scattered excitation light signals.

20. The method of claim 19, wherein a filter is used to distinguish light at the excitation and LIF wavelengths.

21. The method of claim 12, wherein said determining the extent to which the excitation light is attenuated by the ensemble comprises monitoring the intensity of the excitation light entering the ensemble.

22. The method of claim 12, further comprising computing the surface area distribution.

23. The method of claim 22, wherein the surface area distribution is computed from the scattered excitation light signals and the extent to which the excitation light is attenuated by the ensemble.

24. A method of determining surface area distribution within an ensemble of particles, comprising:
    directing a beam of excitation light into the ensemble, the beam propagating along an optical path within the ensemble;
    comparing the intensity of the excitation light exiting the ensemble against the intensity of the excitation light entering the ensemble to determine the extent to which the excitation light is attenuated by particles within the ensemble;
    detecting scattered excitation light originating from various points along the optical path with a detector to generate respective scattered excitation light signals, wherein the scattered excitation light undergoes additional scattering as it propagates away from the optical path and towards the detector used to detect scattered excitation light; and
    computing the surface area distribution of the particles along the optical path using said scattered excitation light signals, while accounting for the attenuation of the excitation light propagating along the optical path and while accounting for said additional scattering of said scattered excitation light.

25. The method of claim 24, wherein laser induced fluorescence (LIF) is generated from particles along the optical path with the excitation light, the method further comprising determining the mass distribution of the particles along the optical path by detecting LIF originating from various points along the optical path with a detector to generate respective LIF signals.

26. The method of claim 25, wherein the LIF undergoes scattering as it propagates away from the optical path and towards the detector used to detect LIF, the method further comprising accounting for said LIF scattering to more accurately calculate the mass distribution of the particles along the optical path.

27. The method of claim 24, comprising correcting the respective scattered excitation light signals for elastic scattered light arriving at the detector which originates from regions outside of the optical path.

28. The method of claim 25, comprising correcting the respective LIF signals for LIF arriving at the detector which originates from regions outside of the optical path.

29. A method of determining the Sauter mean diameter distribution within an ensemble of particles, comprising:

directing a beam of collimated excitation light into the ensemble, the beam propagating along a first optical path within the ensemble;

generating laser induced fluorescence (LIF) from particles along the optical path with the excitation light, the particles scattering and thereby attenuating the excitation light propagating along the optical path;

detecting LIF originating from various points along the optical path with a detector to generate respective LIF signals;

detecting scattered excitation light originating from various points along the optical path with a detector to generate respective scattered excitation light signals; and computing the Sauter mean diameter mass distribution of the particles along the optical path using said LIF signals and said scattered excitation light signals while accounting for the attenuation of the excitation light propagating along the optical path.

30. The method of claim 29, comprising repeating said method for a different region of the ensemble by directing the beam along a second optical path different from the first optical path, wherein the first and second optical paths lie in a common plane and correspond to adjacent regions of the ensemble.

* * * * *